United States Patent
Erver et al.

(10) Patent No.: US 10,981,888 B2
(45) Date of Patent: Apr. 20, 2021

(54) PREPARATION METHOD FOR TRICYCLIC COMPOUNDS

(71) Applicant: BAYER CROPSCIENCE AKTIENGESELLSCHAFT, Monheim am Rhein (DE)

(72) Inventors: Florian Erver, Wiesbaden (DE); Frank Memmel, Guntersblum (DE); Alexander Arlt, Cologne (DE); Werner Hallenbach, Monheim (DE); Tobias Harschneck, Duesseldorf (DE); Christoph Schotes, Duesseldorf (DE); Robert Velten, Langenfeld (DE)

(73) Assignee: Bayer CropScience Aktiengesellschaft, Monheim am Rhein (DE)

(*) Notice: Subject to any disclaimer, the term of this patent is extended or adjusted under 35 U.S.C. 154(b) by 0 days.

(21) Appl. No.: 16/467,101

(22) PCT Filed: Dec. 4, 2017

(86) PCT No.: PCT/EP2017/081343
§ 371 (c)(1),
(2) Date: Jun. 6, 2019

(87) PCT Pub. No.: WO2018/104214
PCT Pub. Date: Jun. 14, 2018

(65) Prior Publication Data
US 2019/0315707 A1    Oct. 17, 2019

(30) Foreign Application Priority Data
Dec. 8, 2016 (EP) .................................. 16202882

(51) Int. Cl.
*C07D 401/04* (2006.01)
*C07D 231/12* (2006.01)
(52) U.S. Cl.
CPC ......... *C07D 401/04* (2013.01); *C07D 231/12* (2013.01)

(58) Field of Classification Search
CPC ................................................... C07D 401/04
USPC ...................................................... 546/275.4
See application file for complete search history.

(56) References Cited

U.S. PATENT DOCUMENTS

| | | | |
|---|---|---|---|
| 9,758,485 B2* | 9/2017 | Hallenbach | A01N 43/56 |
| 10,150,737 B2* | 12/2018 | Hallenbach | A01N 43/56 |
| 2006/0194807 A1* | 8/2006 | Cosford | C07D 401/04 |
| | | | 514/250 |

FOREIGN PATENT DOCUMENTS

WO  2015/067646 A1   5/2015

OTHER PUBLICATIONS

Lennox, Chem. Soc. Rev., 2014, 43, 412.*
International Search Report of International Patent Application No. PCT/EP2017/081343 dated Feb. 23, 2018.
European Search Report of European Patent Application No. 16202882 dated Jan. 31, 2017.

* cited by examiner

*Primary Examiner* — Nizal S Chandrakumar
(74) *Attorney, Agent, or Firm* — McBee Moore & Vanik IP, LLC

(57) ABSTRACT

Methods for preparing compounds of formula (I)

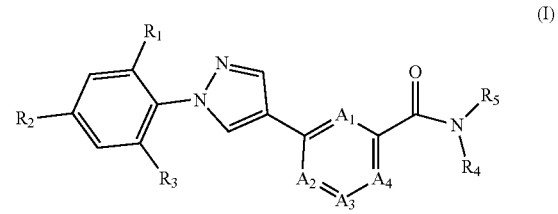

Wherein $R_1$ to $R_5$ and $A_1$ to $A_4$ are as defined in the application.

18 Claims, No Drawings

PREPARATION METHOD FOR TRICYCLIC COMPOUNDS

CROSS-REFERENCE TO RELATED APPLICATIONS

This application is a National Stage entry of International Application No. PCT/EP2017/081343, filed 4 Dec. 2017, which claims priority to European Patent Application No. 16202882.3, filed 8 Dec. 2016.

BACKGROUND

Description of Related Art

The preparation of compounds according to formula (I) is known, for example from WO2015/067646.

SUMMARY

Described herein is a novel method for preparing compounds of the formula (I)

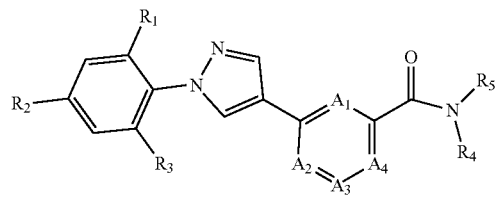

where $R_1$ is halogen, $C_1$-$C_4$-alkyl optionally substituted by halogen or CN or $C_1$-$C_4$-alkoxy optionally substituted by halogen;

$R_2$ is halogen, $C_1$-$C_4$-alkyl optionally substituted by halogen or $C_1$-$C_4$-alkoxy optionally substituted by halogen;

$R_3$ is halogen, $C_1$-$C_4$-alkyl optionally substituted by halogen or CN or $C_1$-$C_4$-alkoxy optionally substituted by halogen;

$R_4$ is hydrogen, $C_1$-$C_4$-alkyl optionally substituted by halogen or CN or $C_3$-$C_6$-cycloalkyl optionally substituted by halogen or CN;

$R_5$ is hydrogen, $C_1$-$C_4$-alkyl optionally substituted by halogen or CN or $C_3$-$C_6$-cycloalkyl optionally substituted by halogen or CN;

$A_1$ is $=C(R_6)-$ or N;

$A_2$ is $=C(R_7)-$ or N;

$A_3$ is $=C(R_8)-$ or N;

$A_4$ is $=C(R_9)-$ or N;

where not more than three of the $A_1$, $A_2$, $A_3$ and $A_4$ substituents are N;

$R_6$, $R_7$, $R_8$ and $R_9$ are each independently hydrogen, $C_1$-$C_4$-alkyl optionally substituted by halogen or CN, or halogen.

DETAILED DESCRIPTION OF A PREFERRED EMBODIMENT

The advantage of this method consists of the fact that it can be carried out as a "one-pot" reaction, i.e. it is not necessary to isolate or purify the intermediate (b) before it is reacted to intermediate (d):

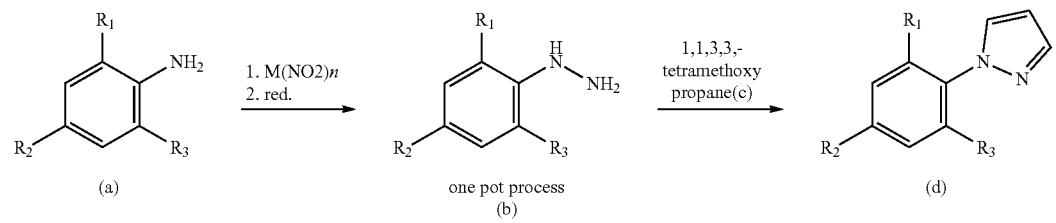

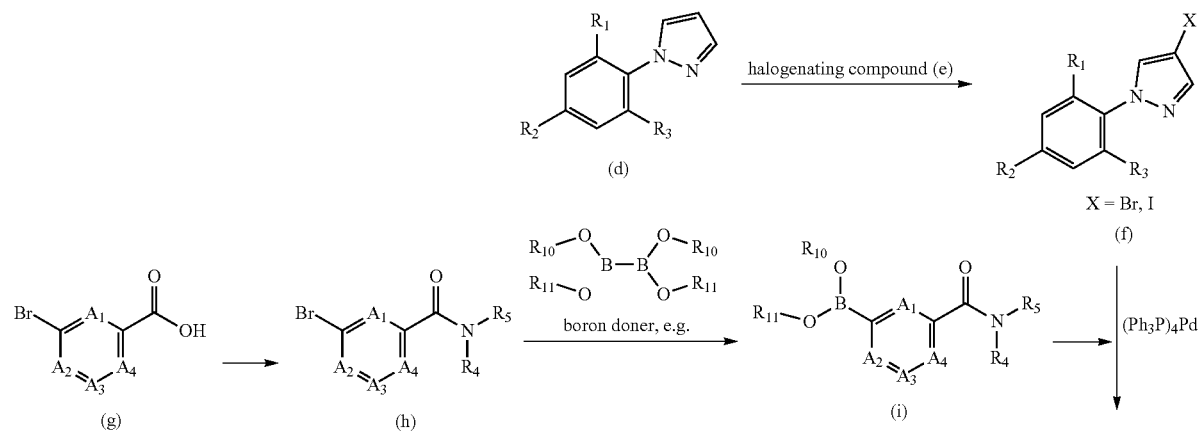

-continued $$(I)$$

where n is one or two and M is ammonium, an alkali metal, preferably Li, K or Na (in the case n=1) or an alkaline earth metal, preferably Mg, Ca or Ba, (in the case n=2). $R_1$, $R_2$, $R_3$, $R_4$, $R_5$ are as defined herein and $R_{10}$ and $R_{11}$ are each independently H or $C_1$-$C_6$-alkyl or $R_{10}$ and $R_{11}$ together are a $C_1$-$C_8$-alkyl bridge (e.g. —$(CH_3)_2C$—$C(CH_3)_2$—).

The preferred embodiments described below refer, if appropriate, to all formulae described herein.

In a preferred embodiment, $A_3$ is C-halogen.
In a preferred embodiment, $A_3$ is N.
In a further preferred embodiment
$A_1$ is =$C(R_6)$—;
$A_2$ is =$C(R_7)$—;
$A_3$ is =$C(R_8)$—; and
$A_4$ is =$C(R_9)$—.

In a further preferred embodiment
$A_1$ is =$C(H)$—;
$A_2$ is =$C(H)$—;
$A_3$ is =$C(R_8)$—; and
$A_4$ is =C(halogen)-, preferably =$C(Cl)$—, =$C(F)$—, =$C(I)$—, =$C(Br)$—, more preferably =$C(Cl)$—.

In a further preferred embodiment
$A_1$ is =$C(R_6)$—;
$A_2$ is =$C(R_7)$—;
$A_3$ is N; and
$A_4$=C(halogen)-, preferably =$C(Cl)$—, =$C(F)$—, =$C(I)$—, =$C(Br)$—, more preferably =$C(Cl)$—.

In a further preferred embodiment
$A_1$ is =$C(H)$—;
$A_2$ is =$C(H)$—;
$A_3$ is N; and
$A_4$=C(halogen)-, preferably =$C(Cl)$—, =$C(F)$—, =$C(I)$—, =$C(Br)$—, more preferably =$C(Cl)$—.

In a further preferred embodiment
$R_1$ is halogen, $C_1$-$C_4$-alkyl optionally substituted by halogen, particularly Br, I, Cl or F, or $C_1$-$C_4$-alkoxy optionally substituted by halogen;
$R_2$ is $C_1$-$C_4$-alkyl substituted by halogen or $C_1$-$C_4$-alkoxy substituted by halogen, in particular Br, I, Cl or F; preferably $C_1$-$C_4$-alkyl substituted by fluorine or $C_1$-$C_4$-alkoxy substituted by fluorine, e.g. perfluoro-$C_1$-$C_4$-alkyl or perfluoro-$C_1$-$C_4$-alkoxy;
$R_3$ is halogen, $C_1$-$C_4$-alkyl optionally substituted by halogen, in particular Br, I, Cl or F, or $C_1$-$C_4$-alkoxy optionally substituted by halogen, in particular Br, I, Cl or F, or CN;
$R_2$ is particularly preferably difluoromethyl, trichloromethyl, chlorodifluoromethyl, dichlorofluoromethyl, trifluoromethyl, 1-fluoroethyl, 2-fluoroethyl, 2,2-difluoroethyl, 2,2,2-trifluoroethyl, 1,2,2,2-tetrafluoroethyl, 1-chloro-1,2,2,2-tetrafluoroethyl, 2,2,2-trichloroethyl, 2-chloro-2,2-difluoroethyl, 1,1-difluoroethyl, pentafluoroethyl, pentafluoro-tert-butyl, heptafluoro-n-propyl, heptafluoroisopropyl, nonafluoro-n-butyl, nonafluoro-sec-butyl, fluoromethoxy, difluoromethoxy, chlorodifluoromethoxy, dichlorofluoromethoxy, trifluoromethoxy, 2,2,2-trifluoroethoxy, 2-chloro-2,2-difluoroethoxy, pentafluoroethoxy, trifluoromethylsulfonyl, trifluoromethylsulfinyl, trifluoromethylsulfanyl; or $C_1$-$C_3$-alkyl substituted by fluorine (preferably perfluorinated $C_1$-$C_3$-alkyl ($CF_3$, $C_2F_5$ or $C_3F_7$)) or $C_1$-$C_3$-alkoxy substituted by fluorine (preferably perfluorinated $C_1$-$C_3$-alkoxy ($OCF_3$, $OC_2F_5$ or $OC_3F_7$)); or perfluorinated $C_1$-$C_3$-alkyl such as perfluorinated n- or i-propyl (—$C_3F_7$), perfluorinated ethyl ($C_2F_5$) or perfluorinated methyl ($CF_3$), particularly preferably perfluorinated n- or i-propyl (—$C_3F_7$) or perfluorinated methyl.

In a further preferred embodiment, $R_1$ and $R_3$ are each independently H, Br, I, Cl or F, cyano, methyl, ethyl, fluoromethyl, difluoromethyl, chlorodifluoromethyl, trifluoromethyl, 2,2,2-trifluoroethyl, methoxy, ethoxy, n-propoxy, 1-methylethoxy, fluoromethoxy, difluoromethoxy, chlorodifluoromethoxy, dichlorofluoromethoxy, trifluoromethoxy, 2,2,2-trifluoroethoxy, 2-chloro-2,2-difluoroethoxy, pentafluoroethoxy.

In a further preferred embodiment, $R_1$ and $R_3$ are each independently H, chlorine, bromine, fluorine, cyano, methyl, ethyl, difluoromethyl, chlorodifluoromethyl, trifluoromethyl, methoxy, ethoxy, 1-methylethoxy, difluoromethoxy, chlorodifluoromethoxy, dichlorofluoromethoxy, trifluoromethoxy, 2,2,2-trifluoroethoxy, 2-chloro-2,2-difluoroethoxy.

In a further preferred embodiment, $R_1$ and $R_3$ are the substituents described herein, but $R_1$ and $R_3$ are not both H in one compound. In other words, if $R_1$ is H in a compound, $R_3$ is one of the other substituents described herein and vice versa.

In a further preferred embodiment, $R_1$ and $R_3$ are each a substituent selected from Cl, Br, F, $C_1$-$C_3$-alkyl, $C_1$-$C_3$-alkyl substituted by halogen, $C_1$-$C_3$-alkoxy or $C_1$-$C_3$-alkoxy substituted by halogen.

In a further preferred embodiment, $R_1$ and $R_3$ are each Cl, Br, are each $C_1$-$C_3$-alkyl, or are each $C_1$-$C_3$-alkyl substituted by halogen, for example perfluorinated $C_1$-$C_3$-alkyl (perfluoromethyl, perfluoroethyl or perfluoropropyl).

In a further preferred embodiment, $R_1$ is perfluorinated $C_1$-$C_3$-alkyl (e.g. perfluoromethyl) and $R_3$ is Cl, Br or F, particularly preferably Cl or Br.

In a further preferred embodiment, $R_4$ is $C_3$-$C_6$-cycloalkyl optionally substituted by Cl, Br, I, F or CN, and $R_5$ is hydrogen or $C_1$-$C_4$-alkyl optionally substituted by halogen or CN and $R_5$ is $C_1$-$C_4$-alkyl optionally substituted by halogen or CN or $C_3$-$C_6$-cycloalkyl optionally substituted by halogen or CN. Further, $R_4$ is cyclopropyl, 1-CN-cyclopropyl and $R_5$ is hydrogen or $C_1$-$C_4$-alkyl such as methyl or ethyl.

The invention also relates to the intermediate (X) and a method for preparing compound (X):

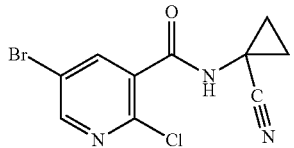
(X)

Furthermore, the invention relates to intermediates (XI) to (XV) and preparation thereof.

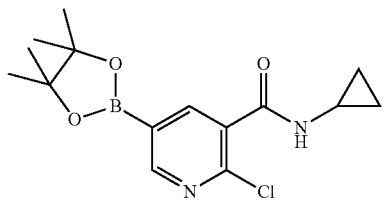
(XI)

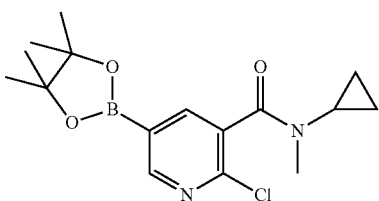
(XII)

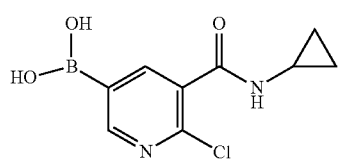
(XIII)

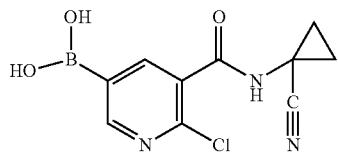
(XIV)

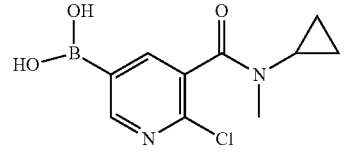
(XV)

The anilines of the formula (a) used as starting materials are known from the literature (e.g. EP2319830, US2002/198399, WO2006137395, WO2009030457, WO2010013567, WO2011009540).

Preference is given here to the following anilines:
4-(1,1,1,2,3,3,3-heptafluoropropan-2-yl)-2,6-dimethylaniline
2,6-dichloro-4-(1,1,1,2,3,3,3-heptafluoropropan-2-yl)aniline
2-chloro-4-(1,1,1,2,3,3,3-heptafluoropropan-2-yl)-6-(trifluoromethyl)aniline
2-chloro-4-(1,1,1,2,3,3,3-heptafluoropropan-2-yl)-6-(trifluoromethoxy)aniline
2-chloro-6-(difluoromethoxy)-4-(1,1,1,2,3,3,3-heptafluoropropan-2-yl)aniline
4-(1,1,1,2,3,3,3-heptafluoropropan-2-yl)-2-methyl-6-(trifluoromethyl)aniline
2-bromo-4-(1,1,1,2,3,3,3-heptafluoropropan-2-yl)-6-(trifluoromethyl)aniline
2-bromo-4-(1,1,1,2,3,3,3-heptafluoropropan-2-yl)-6-(trifluoromethoxy)aniline;

Preferred pyrazoles of the formula (d) are
1-[4-(1,1,1,2,3,3,3-heptafluoropropan-2-yl)-2,6-dimethylphenyl]-1H-pyrazole
1-[2,6-dichloro-4-(1,1,1,2,3,3,3-heptafluoropropan-2-yl)phenyl]-1H-pyrazole
1-[2-chloro-4-(1,1,1,2,3,3,3-heptafluoropropan-2-yl)-6-(trifluoromethyl)phenyl]-1H-pyrazole
1-[2-chloro-4-(1,1,1,2,3,3,3-heptafluoropropan-2-yl)-6-(trifluoromethoxl)phenyl]-1H-pyrazole
1-[2-chloro-6-(difluoromethoxy)-4-(1,1,1,2,3,3,3-heptafluoropropan-2-yl)phenyl]-1H-pyrazole
1-[4-(1,1,1,2,3,3,3-heptafluoropropan-2-yl)-2-methyl-6-(trifluoromethyl)phenyl]-1H-pyrazole
1-[2-bromo-4-(1,1,1,2,3,3,3-heptafluoropropan-2-yl)-6-(trifluoromethyl)phenyl]-1H-pyrazole
1-[2-bromo-4-(1,1,1,2,3,3,3-heptafluoropropan-2-yl)-6-(trifluoromethoxy)phenyl]-1H-pyrazole Preferred halopyrazoles of the formula (e) are
4-bromo-1-[4-(1,1,1,2,3,3,3-heptafluoropropan-2-yl)-2,6-dimethylphenyl]-1H-pyrazole
4-bromo-1-[2,6-dichloro-4-(1,1,1,2,3,3,3-heptafluoropropan-2-yl)phenyl]-1H-pyrazole
4-bromo-1-[2-chloro-4-(1,1,1,2,3,3,3-heptafluoropropan-2-yl)-6-(trifluoromethyl)phenyl]-1H-pyrazole
4-bromo-1-[2-chloro-4-(1,1,1,2,3,3,3-heptafluoropropan-2-yl)-6-(trifluoromethoxy)phenyl]-1H-pyrazole
4-bromo-1-[2-chloro-6-(difluoromethoxy)-4-(1,1,1,2,3,3,3-heptafluoropropan-2-yl)phenyl]-1H-pyrazole
4-bromo-1-[4-(1,1,1,2,3,3,3-heptafluoropropan-2-yl)-2-methyl-6-(trifluoromethyl)phenyl]-1H-pyrazole
4-bromo-1-[2-bromo-4-(1,1,1,2,3,3,3-heptafluoropropan-2-yl)-6-(trifluoromethyl)phenyl]-1H-pyrazole
4-bromo-1-[2-bromo-4-(1,1,1,2,3,3,3-heptafluoropropan-2-yl)-6-(trifluoromethoxl)phenyl]-1H-pyrazole
1-[4-(1,1,1,2,3,3,3-heptafluoropropan-2-yl)-2,6-dimethylphenyl]-4-iodo-1H-pyrazole
1-[2,6-dichloro-4-(1,1,1,2,3,3,3-heptafluoropropan-2-yl)phenyl]-4-iodo-1H-pyrazole
1-[2-chloro-4-(1,1,1,2,3,3,3-heptafluoropropan-2-yl)-6-(trifluoromethyl)phenyl]-4-iodo-1H-pyrazole
1-[2-chloro-4-(1,1,1,2,3,3,3-heptafluoropropan-2-yl)-6-(trifluoromethoxy)phenyl]-4-iodo-1H-pyrazole
1-[2-chloro-6-(difluoromethoxy)-4-(1,1,1,2,3,3,3-heptafluoropropan-2-yl)phenyl]-4-iodo-1H-pyrazole
1-[4-(1,1,1,2,3,3,3-heptafluoropropan-2-yl)-2-methyl-6-(trifluoromethyl)phenyl]-4-iodo-1H-pyrazole
1-[2-bromo-4-(1,1,1,2,3,3,3-heptafluoropropan-2-yl)-6-(trifluoromethyl)phenyl]-4-iodo-1H-pyrazole
1-[2-bromo-4-(1,1,1,2,3,3,3-heptafluoropropan-2-yl)-6-(trifluoromethoxy)phenyl]-4-iodo-1H-pyrazole Particular preference is given here to the following compounds:
2,6-dichloro-4-(1,1,1,2,3,3,3-heptafluoropropan-2-yl)aniline
2-chloro-4-(1,1,1,2,3,3,3-heptafluoropropan-2-yl)-6-(trifluoromethyl)aniline
2-chloro-4-(1,1,1,2,3,3,3-heptafluoropropan-2-yl)-6-(trifluoromethoxy)aniline 2-chloro-6-(difluoromethoxy)-4-(1,1,1,2,3,3,3-heptafluoro-propan-2-yl)aniline
2-bromo-4-(1,1,1,2,3,3,3-heptafluoropropan-2-yl)-6-(trifluoromethyl)aniline
2-bromo-4-(1,1,1,2,3,3,3-heptafluoropropan-2-yl)-6-(trifluoromethoxy)aniline
1-[2,6-dichloro-4-(1,1,1,2,3,3,3-heptafluoropropan-2-yl)phenyl]-1H-pyrazole
1-[2-chloro-4-(1,1,1,2,3,3,3-heptafluoropropan-2-yl)-6-(trifluoromethyl)phenyl]-1H-pyrazole
1-[2-chloro-4-(1,1,1,2,3,3,3-heptafluoropropan-2-yl)-6-(trifluoromethoxl)phenyl]-1H-pyrazole
1-[2-chloro-6-(difluoromethoxy)-4-(1,1,1,2,3,3,3-heptafluoropropan-2-yl)phenyl]-1H-pyrazole
1-[2-bromo-4-(1,1,1,2,3,3,3-heptafluoropropan-2-yl)-6-(trifluoromethyl)phenyl]-1H-pyrazole
1-[2-bromo-4-(1,1,1,2,3,3,3-heptafluoropropan-2-yl)-6-(trifluoromethoxy)phenyl]-1H-pyrazole
4-bromo-1-[2,6-dichloro-4-(1,1,1,2,3,3,3-heptafluoropropan-2-yl)phenyl]-1H-pyrazole
4-bromo-1-[2-chloro-4-(1,1,1,2,3,3,3-heptafluoropropan-2-yl)-6-(trifluoromethyl)phenyl]-1H-pyrazole
4-bromo-1-[2-chloro-4-(1,1,1,2,3,3,3-heptafluoropropan-2-yl)-6-(trifluoromethoxy)phenyl]-1H-pyrazole
4-bromo-1-[2-chloro-6-(difluoromethoxy)-4-(1,1,1,2,3,3,3-heptafluoropropan-2-yl)phenyl]-1H-pyrazole
4-bromo-1-[4-(1,1,1,2,3,3,3-heptafluoropropan-2-yl)-2-methyl-6-(trifluoromethyl)phenyl]-1H-pyrazole
4-bromo-1-[2-bromo-4-(1,1,1,2,3,3,3-heptafluoropropan-2-yl)-6-(trifluoromethyl)phenyl]-1H-pyrazole
4-bromo-1-[2-bromo-4-(1,1,1,2,3,3,3-heptafluoropropan-2-yl)-6-(trifluoromethoxl)phenyl]-1H-pyrazole
1-[2,6-dichloro-4-(1,1,1,2,3,3,3-heptafluoropropan-2-yl)phenyl]-4-iodo-1H-pyrazole
1-[2-chloro-4-(1,1,1,2,3,3,3-heptafluoropropan-2-yl)-6-(trifluoromethyl)phenyl]-4-iodo-1H-pyrazole
1-[2-chloro-4-(1,1,1,2,3,3,3-heptafluoropropan-2-yl)-6-(trifluoromethoxy)phenyl]-4-iodo-1H-pyrazole
1-[2-chloro-6-(difluoromethoxy)-4-(1,1,1,2,3,3,3-heptafluoropropan-2-yl)phenyl]-4-iodo-1H-pyrazole
1-[4-(1,1,1,2,3,3,3-heptafluoropropan-2-yl)-2-methyl-6-(trifluoromethyl)phenyl]-4-iodo-1H-pyrazole
1-[2-bromo-4-(1,1,1,2,3,3,3-heptafluoropropan-2-yl)-6-(trifluoromethyl)phenyl]-4-iodo-1H-pyrazole
1-[2-bromo-4-(1,1,1,2,3,3,3-heptafluoropropan-2-yl)-6-(trifluoromethoxy)phenyl]-4-iodo-1H-pyrazole The starting materials used to prepare the boronates or boronic acids are either commercially available (e.g. 5-bromo-2-chloro-N-cyclopropylnicotinamide, 5-bromo-2-chloro-N-cyclopropyl-N-methylnicotinamide) or can be prepared analogously to the procedure present herein.

Preference is given to preparing the following compounds by the method described herein:

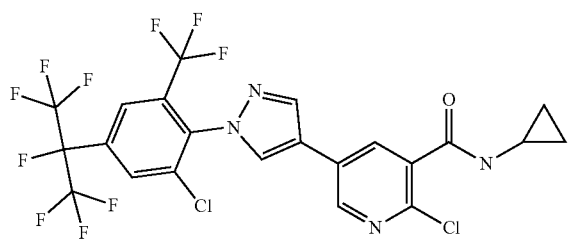

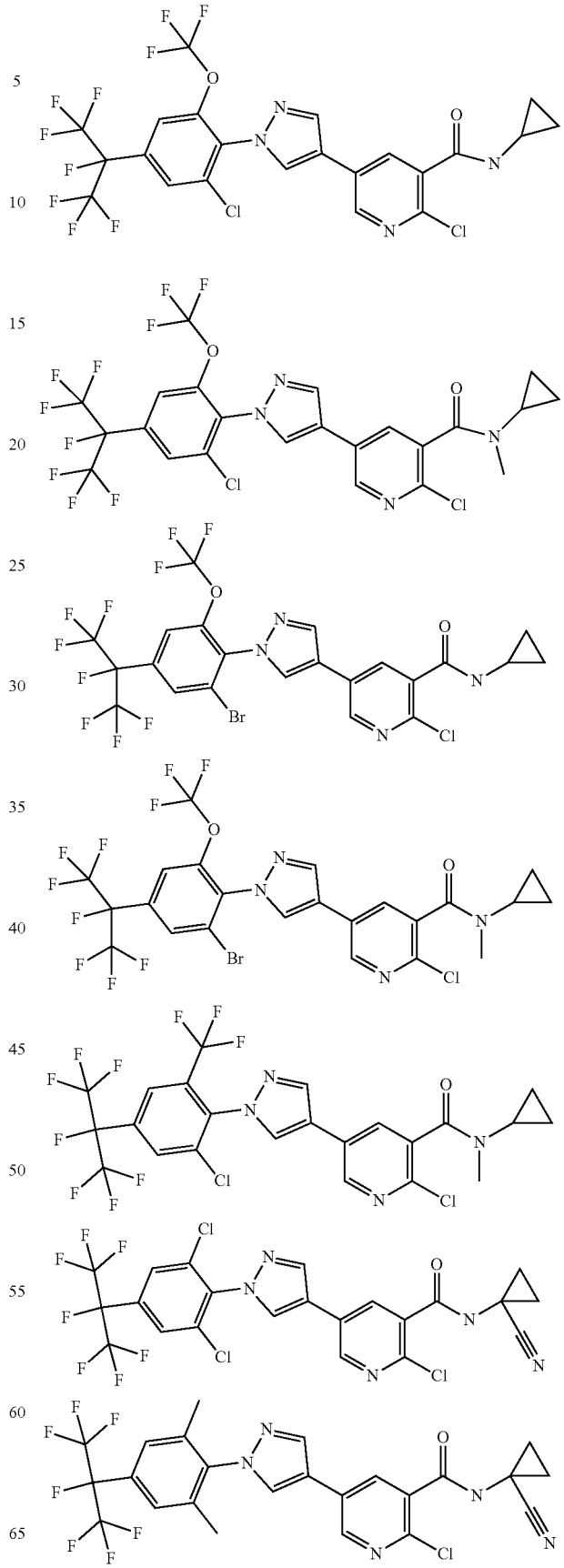

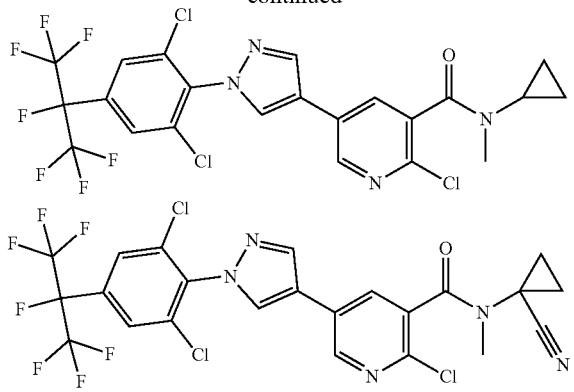

Method Description

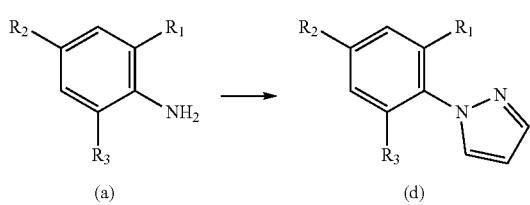

Scheme 1: one pot reaction

The advantage of the present invention is the easy manageability of converting a compound of the formula (a) into a compound of the formula (d). All reaction steps here can be carried out in a one-pot reaction.

The term "one-pot reaction" is understood here to mean the conversion of a compound of the formula (a) to a compound of the formula (d) comprising the steps of diazotization of the compound of the formula (a) (reaction 1), reduction of the resulting salt to give a hydrazine compound of the formula (b) (reaction 2) and cyclization of the resulting compound to give compound (d) (reaction 3), wherein at least one of the following conditions is met:

1) there is no isolation of the diazonium ion (or the corresponding diazonium salt, depending on which counterions are present) from the reaction mixture of reaction 1;
2) there is no purification of the diazonium ion (diazonium salt) from the reaction mixture of reaction 1
   (removal of solvent (actively (e.g. by distillation and/or reduced pressure based on 1013 hPa or precipitation) or optionally by means of the reaction conditions (e.g. evaporation of solvent due to the reaction temperature) is explicitly not purification of the diazonium ion (diazonium salt));
3) there is no isolation of compound (b) from the reaction mixture of reaction 2;
4) there is no purification of a compound (b) from the reaction mixture of reaction 2
   (removal of solvent as used in reaction 1 (actively (e.g. by distillation and/or reduced pressure based on 1013 hPa or precipitation) or optionally by means of the reaction conditions (e.g. evaporation of solvent as used in reaction 1 due to the reaction temperature) is explicitly not purification of the compound of the formula (b));
5) all reactions 1, 2 and 3 are carried out in the same reaction vessel,
6) from the solvent of reaction 1 only a small proportion, if any, of the solvent is removed prior to the start of the second reaction or prior to the start of reaction 3, preferably less than 50% by volume (percent by volume based on the volume of solvent used), preferably less than 30% by volume, more preferably less than 10% by volume, even more preferably at most 5% by volume of the solvent (e.g. by evaporation, for example at a reaction temperature of about 40° C., or active removal, e.g. by distillation and/or reduced pressure based on 1013 hPa), preferably no solvent is actively removed by solvent exchange between reaction 1 and reaction 2 and between reaction 2 and 3 (e.g. by distillation and/or reduced pressure based on 1013 hPa);
7) there is essentially no exchange of solvent between reaction 1 and 2 and no exchange of solvent between reaction 2 and 3, i.e. if any, at most 50% by volume, preferably at most 40% by volume, more preferably at most 30% by volume, even more preferably at most 20% by volume of the solvent used prior to reaction 1 is replaced by a new solvent (the new solvent can be the same solvent or another solvent).

During the reaction sequence in a "one-pot" reaction, reaction volumes are added in the form of solids, liquids or suspensions, for example in the form of solid, dissolved or suspended reducing agent, or solvent (the same solvent as used in reaction 1 or another solvent), but with the aim of a reaction sequence without essential/without exchange of solvent as used in reaction 1 or active removal of solvent as used in reaction 1.

Preferably, neither the diazonium ion (diazonium salt) formed from compound (a) nor compound (b) are isolated or purified during the reaction sequence which leads to compound (d).

Further preferably, neither the diazonium ion (diazonium salt) formed from compound (a) nor compound (b) are isolated or purified during the reaction sequence which leads to compound (d), nor is there an essential removal and/or exchange of solvent, for example of the solvent as used in reaction 1.

Further preferably, neither the diazonium ion (diazonium salt) formed from compound (a) nor compound (b) are isolated or purified during the reaction sequence which leads to compound (d), nor is there an essential removal and/or exchange of solvent, for example of the solvent as used in reaction 1 and all of reactions 1, 2 and 3 are carried out in the same reaction vessel. In this case, those skilled in the art choose a reaction vessel from the start that can accommodate all volumes for reactions 1, 2 and 3.

In other words, it is preferable that the reaction sequence is a telescoped reaction in one or more vessels, preferably one vessel.

In the context of the present invention, the term "purification" refers to the enrichment of a substance (and therefore depletion of other substances) to a purity of at least 20% by weight (percent by weight of a substance based on the total mass measured. The percentage may be determined chromatographically for example (e.g. HPLC or gas chromatographically or gravimetrically)), and is preferably at least 50% by weight, even more preferably at least 75% by weight, e.g. 90% by weight, 98% by weight or greater than 99% by weight.

N-arylpyrazoles of the formula (d) are prepared by diazotizing 2,4,6-trisubstituted anilines of the formula (a) with a stoichiometric amount of nitrite, by reduction to the corresponding hydrazine intermediate of the formula (b) by adding a reducing agent and which is then reacted by adding stoichiometric amounts of 1,1,3,3-tetramethoxypropane (c) in the presence of a solvent.

Suitable nitrites are, for example, alkali metal or alkaline earth metal nitrites or ammonium nitrite. Preference is given to $LiNO_2$, $NaNO_2$, $KNO_2$, $Mg(NO_2)_2$, $Ca(NO_2)_2$ or $Ba(NO_2)_2$, particular preference being given to $LiNO_2$ $NaNO_2$, $KNO_2$, very particular preference being given to $NaNO_2$.

Suitable solvents are, e.g.: carboxylic acids (such as acetic acid, n-propanoic acid, n-butanoic acid), ethers (such as tetrahydrofuran, 1,2-dimethoxyethane, 1,4-dioxane) and nitriles (such as acetonitriles), or mixtures of these specified solvents.

Preferred solvents are carboxylic acids. Very particular preference is given to acetic acid.

Particularly suitable as reducing agents are: tin(II) salts (such as tin(II) chloride, tin(II) bromide and tin(II) iodide) and sulfites (such as lithium sulfite, sodium sulfite and potassium sulfite). Particular preference is given to the use of all tin(II) salts mentioned. The use of tin(II) chloride is especially preferred.

The reaction of compounds of the formula (a) with nitrite is carried out preferably at an ambient temperature in the range of 0° C. to 80° C., such as in the range of 10° C. to 60° C., more preferably in the range of 20° C. to 50° C. (e.g. in the range of 20° C. to 40° C.).

The reduction reaction of compounds of the formula (b) with a reducing agent is preferably carried out at an ambient temperature in the range of 0° C. to 80° C., such as in the range of 10° C. to 60° C. (e.g. 10° C. to 35° C.).

The ring closure reaction with 1,1,3,3-tetramethoxypropane is preferably carried out at an ambient temperature in the range of 0° C. to 80° C., more preferably in the range of 10° C. to 60° C., even more preferably in the range of 20° C. to 50° C.

All three of these reactions are preferably conducted in the range of standard pressure (1013 hPa), e.g. in the range of 300 hPa to 5000 hPa or 500 hPa to 2000 hPa, preferably such as in the range of 1013 hPa+200 hPa.

The reaction time of the compounds of the formula (a) with nitrite is preferably in the range of the metering time of the nitrite in an appropriate acid such as sulfuric acid. The reaction is instantaneous. Those skilled in the art can estimate the metering time without problems based on experience. However, preference is given to at least half an hour, such as in the range of 0.5 h to 3 h, e.g. 1 h+0.5 h.

The reaction time of the compounds of the formula (b) with a reducing agent is preferably in the range of the metering time of at least 5 min., such as around at least 15 min., at least 30 min. or at least 1 hour.

The reaction time of the ring closure reaction is preferably in the range of 0.05 to 30 hours, more preferably in the range of 0.5 to 20 hours, still more preferably in the range of 2 to 15 hours, such as, for example, in the range of 4 to 8 hours.

A preferred embodiment of the method according to the invention is as follows: The compounds of the formula (a) are initially charged in an organic solvent and sodium nitrite is added, for example dissolved in a strong acid such as concentrated sulfuric acid. After the reaction is complete, a solution of the reducing agent is added to the reaction mixture, for example in a strong acid such as concentrated hydrochloric acid or sulfuric acid, preferably hydrochloric acid. After the reaction is complete, 1,1,3,3-tetramethoxypropane is added to the reaction mixture. Subsequently, the reaction mixture is preferably incubated with vigorous stirring in a temperature range of 15° C. to 60° C., more preferably in a temperature range of 25° C. to 50° C., for a period of 4 to 8 hours until conversion is complete.

An especially preferred embodiment of the method according to the invention is as follows: The compound of formula (a) is initially charged in acetic acid and sodium nitrite is added dissolved in concentrated sulfuric acid. After the reaction is complete, a solution of tin(II) chloride in concentrated hydrochloric acid is added to the reaction mixture. After the reaction is complete, 1,1,3,3-tetramethoxypropane is added to the reaction mixture. Subsequently, the reaction mixture is preferably incubated with vigorous stirring in a temperature range of 15° C. to 60° C., more preferably in a temperature range of 25° C. to 50° C., for a period of 4 to 8 hours until conversion is complete.

The compound of the formula (d) can be worked-up and isolated, for example, by introducing the reaction mixture into deionised water.

The product can be further extracted into a water-insoluble organic phase, in isopropyl acetate/n-heptane 1:1 (v/v) for example, and the organic phase washed with an aqueous acid, such as 10% aqueous hydrochloric acid, and saturated sodium chloride solution. After drying the organic phase, e.g. over magnesium sulfate, and filtration of the drying agent, the solvent can be removed, for example distilled off under reduced pressure; the residue can be subjected to a vacuum distillation at 0.05-0.10 mbar in a split-tube column.

Scheme 2: Preparation of compounds of the formula (f)

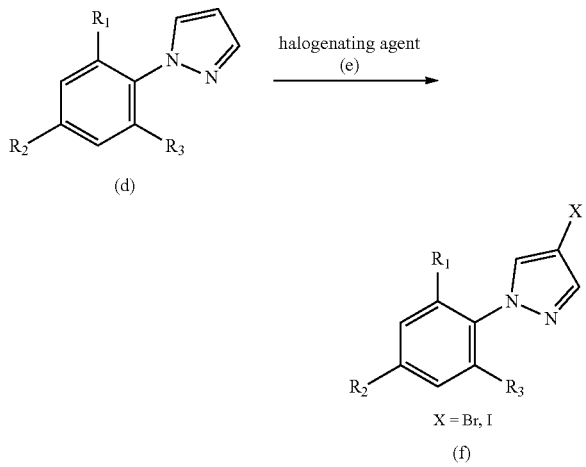

The radicals $R_1$, $R_2$ and $R^3$ have the meanings described above. X is, for example, bromine or iodine. The compounds of the structural formula (f) are, for example, the compounds stated above as preferred halopyrazoles:

4-bromo-1-[4-(1,1,1,2,3,3,3-heptafluoropropan-2-yl)-2,6-dimethylphenyl]-1H-pyrazole 4-bromo-1-[2,6-dichloro-4-(1,1,1,2,3,3,3-heptafluoropropan-2-yl)phenyl]-1H-pyrazole 4-bromo-1-[2-chloro-4-(1,1,1,2,3,3,3-heptafluoropropan-2-yl)-6-(trifluoromethyl)phenyl]-1H-pyrazole 4-bromo-1-[2-chloro-4-(1,1,1,2,3,3,3-heptafluoropropan-2-yl)-6-(trifluoromethoxy)phenyl]-1H-pyrazole 4-bromo-1-[2-chloro-6-(difluoromethoxy)-4-(1,1,1,2,3,3,3-heptafluoropropan-2-yl)phenyl]-1H-pyrazole 4-bromo-1-[4-(1,1,1,2,3,3,3-heptafluoropropan-2-yl)-2-methyl-6-(trifluoromethyl)phenyl]-1H-pyrazole 4-bromo-1-[2-bromo-4-(1,1,1,2,3,3,3-heptafluoropropan-2-yl)-6-(trifluoromethyl)phenyl]-1H-pyrazole
4-bromo-1-[2-bromo-4-(1,1,1,2,3,3,3-heptafluoropropan-2-yl)-6-(trifluoromethoxl)phenyl]-1H-pyrazole
1-[4-(1,1,1,2,3,3,3-heptafluoropropan-2-yl)-2,6-dimethylphenyl]-4-iodo-1H-pyrazole
1-[2,6-dichloro-4-(1,1,1,2,3,3,3-heptafluoropropan-2-yl)phenyl]-4-iodo-1H-pyrazole
1-[2-chloro-4-(1,1,1,2,3,3,3-heptafluoropropan-2-yl)-6-(trifluoromethyl)phenyl]-4-iodo-1H-pyrazole
1-[2-chloro-4-(1,1,1,2,3,3,3-heptafluoropropan-2-yl)-6-(trifluoromethoxy)phenyl]-4-iodo-1H-pyrazole
1-[2-chloro-6-(difluoromethoxy)-4-(1,1,1,2,3,3,3-heptafluoropropan-2-yl)phenyl]-4-iodo-1H-pyrazole
1-[4-(1,1,1,2,3,3,3-heptafluoropropan-2-yl)-2-methyl-6-(trifluoromethyl)phenyl]-4-iodo-1H-pyrazole
1-[2-bromo-4-(1,1,1,2,3,3,3-heptafluoropropan-2-yl)-6-(trifluoromethyl)phenyl]-4-iodo-1H-pyrazole
1-[2-bromo-4-(1,1,1,2,3,3,3-heptafluoropropan-2-yl)-6-(trifluoromethoxy)phenyl]-4-iodo-1H-pyrazole Compounds according to the invention of the general structure (f) are prepared by reacting the pyrazoles of the structure (d) with halogenating agents. The $R_1$-$R_3$ radicals are as defined above. Suitable halogenating compounds are known to those skilled in the art, such as bromine, iodine, an inorganic bromine or iodine salt or an organic bromine or iodine molecule in which the bond of an organic radical to the bromine or iodine is polarized such that the bromine or iodine is a carrier of a partial positive charge, preference being given to e.g. bromine, iodine, N-bromosuccinimide, N-iodosuccinimide, 1,3-dibromo-5-5-dimethylhydantoin and iodine monochloride. Preference is given to using bromine, iodine and iodosuccinimide. It may be advantageous to conduct the reaction in the presence of an oxidizing agent, e.g. hydrogen peroxide.

The reaction can be carried out within a wide temperature range. Usually, it is conducted within a temperature range of −78° C. to 200° C., preferably at temperatures between −10 to 150° C., such as, for example between 60° C. and 100° C.

The reaction can be carried out at elevated or else reduced pressure. However, it is preferably conducted at standard pressure, e.g. in the range of 1013 hPa±300 hPa, or in the range of 1013 hPa±100 hPa, or in the range of 1013 hPa±50 hPa.

Suitable diluents or solvents for carrying out the processes according to the invention are, in principle, all organic solvents which are inert under the specific reaction conditions. Examples include: halohydrocarbons (e.g. chlorohydrocarbons such as tetrachloroethane, dichloropropane, methylene chloride, dichlorobutane, chloroform, carbon tetrachloride, trichloroethane, trichloroethylene, pentachloroethane, difluorobenzene, 1,2-dichloroethane, chlorobenzene, bromobenzene, dichlorobenzene, chlorotoluene, trichlorobenzene), alcohols (e.g. methanol, ethanol, isopropanol, butanol), nitriles such as acetonitrile, propionitrile, butyronitrile, isobutyronitrile, benzonitrile, m-chlorobenzonitrile). Aliphatic, cycloaliphatic or aromatic hydrocarbons (e.g. pentane, hexane, heptane, octane, nonane and industrial hydrocarbons), cyclohexane, methylcyclohexane, petroleum ether, ligroin, octane, benzene, toluene, chlorobenzene, bromobenzene, nitrobenzene, xylene, esters (e.g. methyl, ethyl, butyl or isobutyl acetate, dimethyl carbonate, dibutyl carbonate, ethylene carbonate); amides (e.g. N,N-dimethylformamide, N,N-dipropylformamide, N,N-dibutylformamide, N-methylpyrrolidine.

Preferred diluents used may be any solvent that does not interfere with the reaction, for example water. Useful are aromatic hydrocarbons such as benzene, toluene, xylene or chlorobenzene; halogenated hydrocarbons such as dichloromethane, chloroform, 1,2-dichloroethane or carbon tetrachloride; esters such as ethyl acetate and butyl acetate; amides such as dimethylformamide and dimethylacetamide, N-methylpyrrolidinone; nitriles such as acetonitrile or propionitrile; the solvents can be used individually or in combination of 2 or more. In a preferred embodiment, the solvent is a nitrile, for example, acetonitrile.

The compounds of the structural formula (d) are, for example, the compounds stated above as preferred pyrazoles for example:

1-[4-(1,1,1,2,3,3,3-heptafluoropropan-2-yl)-2,6-dimethylphenyl]-1H-pyrazole
1-[2,6-dichloro-4-(1,1,1,2,3,3,3-heptafluoropropan-2-yl)phenyl]-1H-pyrazole
1-[2-chloro-4-(1,1,1,2,3,3,3-heptafluoropropan-2-yl)-6-(trifluoromethyl)phenyl]-1H-pyrazole
1-[2-chloro-4-(1,1,1,2,3,3,3-heptafluoropropan-2-yl)-6-(trifluoromethoxyphenyl]-1H-pyrazole
1-[2-chloro-6-(difluoromethoxy)-4-(1,1,1,2,3,3,3-heptafluoropropan-2-yl)phenyl]-1H-pyrazole
1-[4-(1,1,1,2,3,3,3-heptafluoropropan-2-yl)-2-methyl-6-(trifluoromethyl)phenyl]-1H-pyrazole
1-[2-bromo-4-(1,1,1,2,3,3,3-heptafluoropropan-2-yl)-6-(trifluoromethyl)phenyl]-1H-pyrazole
1-[2-bromo-4-(1,1,1,2,3,3,3-heptafluoropropan-2-yl)-6-(trifluoromethoxy)phenyl]-1H-pyrazole Particular catalysts are not necessary for this reaction. In certain circumstances, trifluoromethanesulfonic acid for example may be used in stoichiometric amounts for the activation, but this is not strictly necessary in the reactions claimed herein.

As halogenating agent (e), known iodine/bromine donors may be used. Non-limiting examples are bromine, 1,3,5-tribromo-1,3,5-triazinane-2,4,6-trione, N-iodosuccinimide and 1,3-dibromo-5,5-dimethylhydantoin, preferred halogenating agents being N-iodosuccinimide and 1,3-dibromo-5,5-dimethylhydantoin.

Scheme 3: Preparation of compounds of the formula (h)

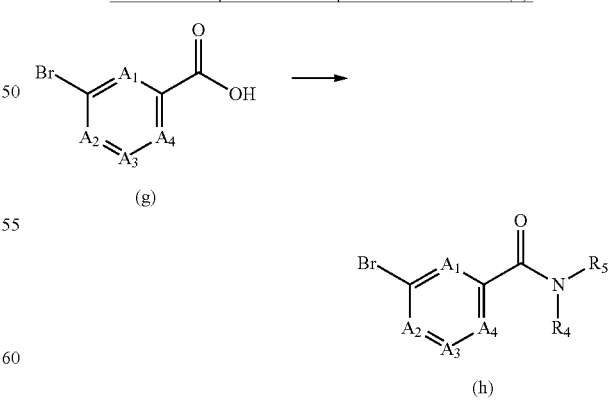

Compounds of the formula (h) may be prepared from compounds of the formula (g) by activation to the corresponding carbonyl halide (k) and reaction thereof with an amine:

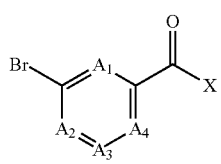

(k)

where X is a halogen such as F, Cl, Br or I, preferably Cl, and $A_1$ to $A_4$ are defined as described herein.

The carbonyl halides may be obtained in customary fashion by reacting a carboxylic acid of the structure (g) with suitable halogenating reagents. For example, inorganic acid halides may be used for the halogenation reaction such as thionyl chloride, thionyl bromide, oxalyl chloride, phosphorus trihalides or phosphorus pentahalides, wherein the chlorides are preferred (Houben-Weyl, Methoden der organischen Chemie [Methods of Organic Chemistry], Vol. VIII, 4th edition, 1952, G. Thieme Verlag Stuttgart-New York, pp. 359, 463 ff.). The reaction can be carried with or without additional diluent.

The compounds of the formula (g) are known and may also be purchased commercially. Preferred compounds of the formula (g) are, for example: 2-Chloro-5-bromobenzoic acid and 2-chloro-5-bromopyridine-3-carboxylic acid.

1-10 mol, preferably 1-5 mol of halogenating reagent are used per 1 mol of the formula (g).

The reaction can be carried out within a wide temperature range. Usually, it is conducted within a temperature range from −78° C. to 200° C., preferably at temperatures between −10 to 150° C.

The reaction can be carried out at elevated or else reduced pressure. However, it is preferably conducted at standard pressure, e.g. in the range of 1013 hPa±300 hPa, or in the range of 1013 hPa±100 hPa, or in the range of 1013 hPa±50 hPa.

Any solvent that does not interfere with the reaction may be used as preferred diluent. Useful are aromatic hydrocarbons such as benzene, toluene, xylene or chlorobenzene; halogenated hydrocarbons such as dichloromethane, chloroform, 1,2-dichloroethane or carbon tetrachloride; esters such as ethyl acetate and butyl acetate; the solvents can be used individually or in combination of 2 or more.

Generally, the reaction can be carried out without adding a catalyst. It may be advantageous, however, to catalyse the reaction by adding amides such as dimethylformamide and dimethylacetamide.

Compounds of the formula (h) may be prepared from compounds of the formula (k) by reaction with an amine. The reaction may be carried out with or without diluent and with or without the presence of basic reaction auxiliaries.

1-5, preferably 1-2.5 mol of amine and possibly 0-10 mol, preferably 1-1.5 mol of basic reaction auxiliary are used per 1 mol of the compound (k).

The preparation of the compounds of the formula (k) is further described above. Preferred compounds of the formula (h) are, for example, 2-chloro-5-bromobenzoyl chloride and 2-chloro-5-bromopyridine-3-carbonyl chloride.

The amines used in the reaction are known and may also be purchased commercially. Preference is given to, e.g. cyclopropylamine, 1-cyanocyclopropylamine, N-methylcyclopropylamine and 1-cyano-N-methylcyclopropylamine.

The basic reaction auxiliaries used to carry out the method according to the invention may be all suitable acid binders. Examples include alkaline earth metal or alkali metal compounds (e.g. hydroxides, hydrides, oxides and carbonates of lithium, sodium, potassium, magnesium, calcium and barium), amines, in particular tertiary amines, (e.g. triethylamine, trimethylamine, tribenzylamine, triisopropylamine, tributylamine, N,N-dimethylaniline, N,N-dimethyltoluidine, pyridine, 4-pyrrolidinopyridine, 4-dimethylaminopyridine, N-propyldiisopropylamine, N-ethyldiisopropylamine, N-methylmorpholine, N-ethylmorpholine).

The activation of the compounds of the formula (g) and the reaction with amines can also be carried out successively in a one-pot reaction.

Scheme 4: Preparation of compounds of the formula (i)

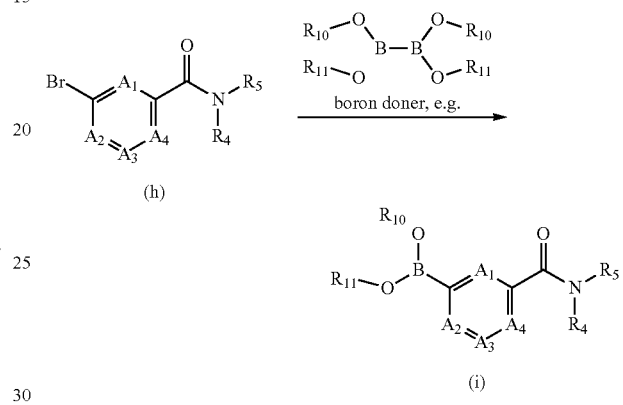

The radicals $R_4$, $R_5$, $R_{10}$, $R_{11}$ and $A_1$-$A_4$ are defined as described above. Preferred compounds of the structural formula (i) are, for example, the intermediates (XI) and (XV) described above.

Compounds of the general structure (i) according to the invention are prepared by reacting bromides of the general structure (h) in the presence of a suitable catalyst, for example a palladium catalyst, and a suitable base with a boron donor such as bis(pinacolato)diboron

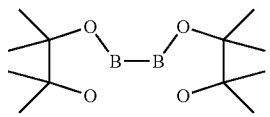

or tetrahydroxydiboron.

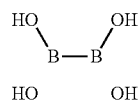

In general, a palladium catalyst can be used for this reaction. Preference is given to the following palladium catalysts:
tetrakis(triphenylphosphine)palladium(0), bis(triphenylphosphine)palladium(II) chloride, ([1,1'-bis(diphenylphosphino)ferrocene]dichloropalladium(II), ([1,1'-bis(diphenylphosphino)ferrocene]dichloropalladium(II) dichloromethane complex, (2-dicyclohexylphosphino-2',4',6'-triisopropyl-1,1'-biphenyl) [2-(2-aminoethyl)phenyl)]palladium(II) chloride and chloro[(di(1-adamantyl)-N-butylphosphino)-2-(2-aminobiphenyl)]palladium(II) (cataCXium® A Pd G2).

In the case of using bis(pinacolato)diboron, preference is given to using as palladium catalyst, e.g. tetrakis(triphenylphosphine)palladium(0), bis(triphenylphosphin)palladium(II) chloride, ([1,1'-bis(diphenylphosphino)ferrocene)]dichloropalladium(II) and ([1,1'-bis(diphenylphosphino)ferrocene)]dichloropalladium(II) dichloromethane complex. Particular preference is given to using bis(triphenylphosphine)palladium(II) chloride), ([1,1'-bis(diphenylphosphino)ferrocene)]dichloropalladium(II) and ([1,1'-bis(diphenylphosphino)ferrocene)]dichloropalladium(II) dichloromethane complex.

Suitable diluents or solvents for carrying out the method according to the invention are, in principle, all organic solvents which are inert under the specific reaction conditions. It is also possible to use these as mixtures. Examples include: 1,4-dioxane, tetrahydrofuran, ethylene glycol dimethyl ether, dimethylformamide, dimethyl sulfoxide, acetonitrile, dichloromethane, toluene. In the case of using bis(pinacolato)diboron preference is given to using 1,4-dioxane while in the case of using tetrahydroxydiboron preference is given to using methanol.

Scheme 5: Preparation of compounds of the formula (I)

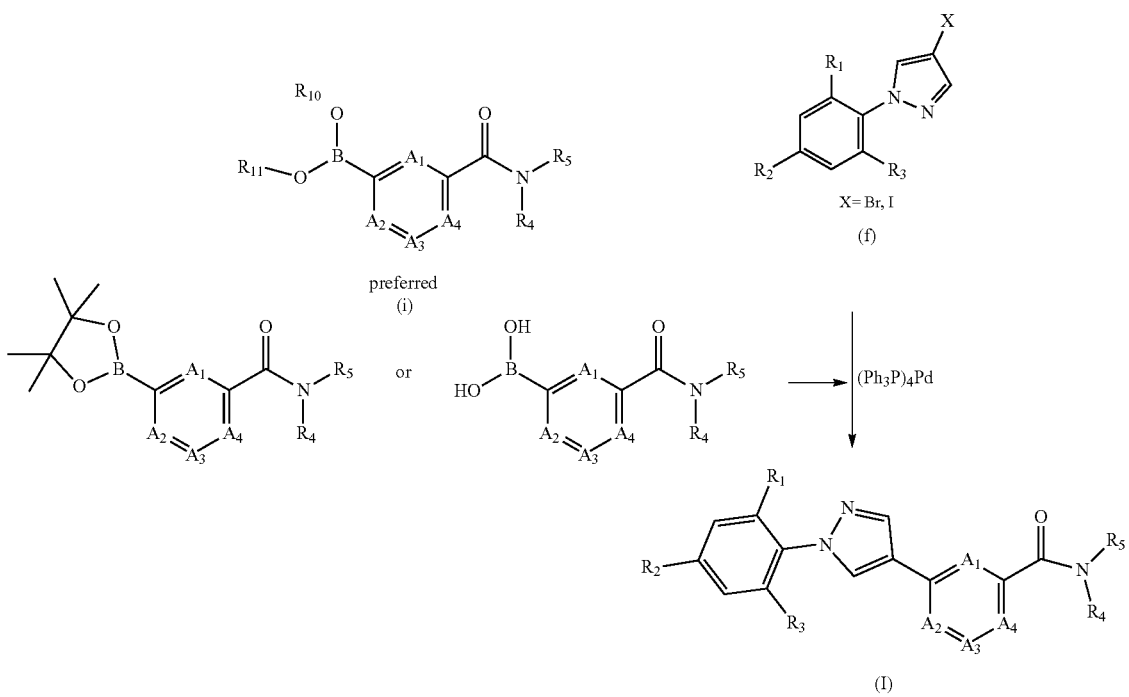

In the case of using tetrahydroxydiboron, preference may be given to using as palladium catalyst, e.g. (2-dicyclohexylphosphino-2',4',6'-triisopropyl-1,1'-biphenyl) [2-(2-aminoethyl)phenyl)]palladium(II) chloride, ([1,1'-bis(diphenylphosphino)ferrocene)]dichloropalladium(II) dichloromethane complex, ([1,1'-bis(diphenylphosphino)ferrocene)]dichloropalladium(II) and chloro [(di(1-adamantyl)-N-butylphosphino)-2-(2-aminobiphenyl)]palladium(II) (cata CXium® A Pd G2). Particular preference is given to using ([1,1'-bis(diphenylphosphino)ferrocene)]dichloropalladium(II) dichloromethane complex and chloro[(di(1-adamantyl)-N-butylphosphino)-2-(2-aminobiphenyl)]palladium(II) (cataCXium® A Pd G2).

Suitable bases are known to those skilled in the art, such as potassium acetate, sodium acetate, potassium carbonate, caesium carbonate and triethylamine. Preference is given to using potassium acetate.

The reaction can be carried out within a wide temperature range. Usually, it is conducted in a temperature range of 0° C. to 200° C., preferably at temperatures of 15 to 150° C.

The reaction can be carried out at elevated or else reduced pressure. However, it is preferably conducted at standard pressure, e.g. in the range of 1013 hPa±300 hPa, or in the range of 1013 hPa±100 hPa, or in the range of 1013 hPa±50 hPa.

The radicals $R_1$-$R_5$ and $A_1$-$A_4$ are defined as described above. X is, for example, bromine or iodine. The compounds of the structural formula (i) are, for example, the intermediates (XI) to (XV) described above.

Compounds of the general structure (i) according to the invention are prepared by reacting halides of the general structure (f), in the presence of a suitable palladium catalyst and a suitable base, with a boronic acid derivative of the general structure (i).

Suitable palladium catalysts are, for example, tetrakis(triphenylphosphine)palladium(0) and bis(triphenylphosphine)palladium(II) chloride. Preference is given to using tetrakis(triphenylphosphine)palladium(0).

Suitable bases are known to those skilled in the art, such as sodium carbonate, potassium carbonate, caesium carbonate, sodium hydrogencarbonate and potassium phosphate. Preference is given to using potassium carbonate.

The reaction can be carried out within a wide temperature range. Usually, it is conducted in a temperature range of 0° C. to 200° C., preferably at temperatures of 15° C. to 150° C.

The reaction can be carried out at elevated or else reduced pressure. However, it is preferably conducted at standard pressure, e.g. in the range of 1013 hPa±300 hPa, or in the range of 1013 hPa±100 hPa, or in the range of 1013 hPa±50 hPa.

Suitable diluents or solvents for carrying out the method according to the invention are, in principle, all organic solvents which are inert under the specific reaction conditions. It is also possible to use these as mixtures. Examples include: methanol, ethanol, 2-propanol, water, 1,4-dioxane, tetrahydrofuran and dimethylformamide. Preference is given to using 2-propanol.

Scheme 5b: Preparation of compounds of the formula (Ib)

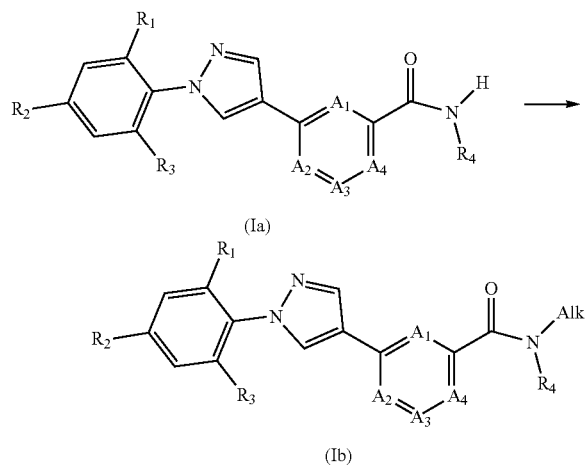

The radicals $R_1$-$R_4$ and $A_1$-$A_4$ are defined as described above, Alk is $C_1$-$C_4$-alkyl optionally substituted by halogen (preferably F, Cl, Br or I) or CN, wherein in the case of halogen-substituted $C_1$-$C_4$-alkyl one, or more than one, H up to all H (perhalogenated) may be replaced by halogen. In the case of CN-substituted $C_1$-$C_4$-alkyl, preferably only one H is replaced by a CN group.

Compounds of the general structure (Ib) according to the invention may also be prepared by deprotonating secondary amides of the general structure (Ia) with a suitable base and subsequently by reacting with a suitable electrophile. Alternatively, these compounds may also be prepared according to the method described under 5. Preference is given to using sodium hydride as base. Suitable electrophiles are, for example, alkyl halides such as methyl iodide and methyl bromide. Preference is given to using methyl iodide.

The reaction can be carried out within a wide temperature range. Usually, it is conducted in a temperature range of −78° C. to 150° C., preferably at temperatures of −40° C. to 100° C.

The reaction can be carried out at elevated or else reduced pressure. However, it is preferably conducted at standard pressure, e.g. in the range of 1013 hPa±300 hPa, or in the range of 1013 hPa±100 hPa, or in the range of 1013 hPa±50 hPa.

Suitable diluents or solvents for carrying out the method according to the invention are, in principle, all organic solvents which are inert under the specific reaction conditions. It is also possible to use these as mixtures. Examples include: dimethylformamide, acetonitrile, dimethyl sulfoxide, tetrahydrofuran and dichloromethane. Preference is given to using tetrahydrofuran.

EXAMPLES

The examples which follow illustrate the method according to the invention in detail.

Preparation of Compounds of the Formula (i) with bis(pinacolato)diboron

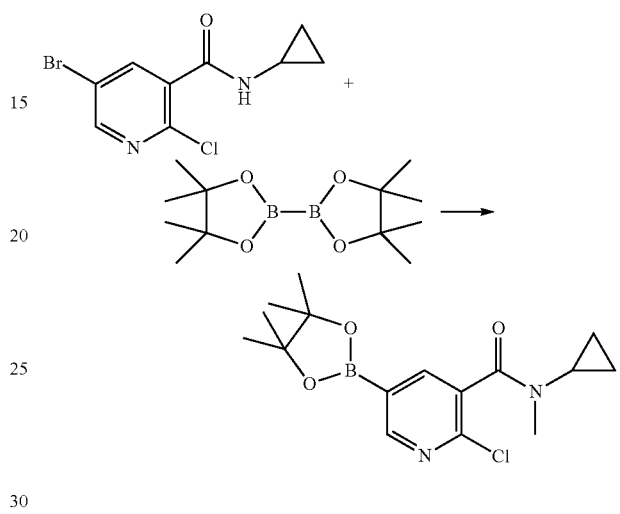

20 g (72.5 mmol) of 5-bromo-2-chloro-N-cyclopropylnicotinamide in 272 ml of dioxane were initially charged in a 500 ml flask and 20.3 g (80 mmol) of bispinacolatodiboron, 28.5 g (290 mmol) of anhydrous potassium acetate and 4 g (4.9 mmol) of ([1,1'-bis(diphenylphosphino)ferrocene)]dichloropalladium(II) dichloromethane complex were added. The mixture was then stirred at 80° C. for 4 hours. The mixture was then cooled, filtered through kieselguhr, and the filter cake was washed with a little ethyl acetate. The filtrate was concentrated under reduced pressure on a rotary evaporator. The residue was taken up in methyl t-butyl ether and 10% aqueous sodium hydroxide solution was added. Undissolved constituents were filtered off and the phases then separated. The organic phase was post-extracted once with 10% aqueous sodium hydroxide solution. The combined aqueous phases were washed with methyl t-butyl ether, then acidified with cooling with concentrated aqueous hydrochloric acid and extracted three times with ethyl acetate. The combined organic phases were washed with saturated aqueous sodium chloride solution, dried with sodium sulphate and concentrated on a rotary evaporator under reduced pressure. 15.9 g of residue were obtained.

12.4 g of the residue were stirred for one hour with 13 ml of 10% aqueous sodium hydroxide solution and subsequently extracted three times each with 15 ml of dichloromethane. The aqueous phase was then acidified with concentrated aqueous hydrochloric acid. A pale brown solid precipitated which was filtered off with suction, washed with a little water and dried in air. 3.85 g of 2-chloro-N-cyclopropyl-5-(4,4,5,5-tetramethyl-1,3,2-dioxaborolan-2-yl)nicotinamide were obtained.

HPLC-MS[b)]: log P=0.90, mass (m/z)=323 [M+H]$^+$.

$^1$H-NMR (400 MHz, d$_6$-DMSO): δ=8.62 (s, 1H), 7.95 (s, 1H), 3.04 (s, 3H), 2.65-2.70 (m, 1H), 1.14 (s, 12H), 0.45-0.55 (m, 4H).

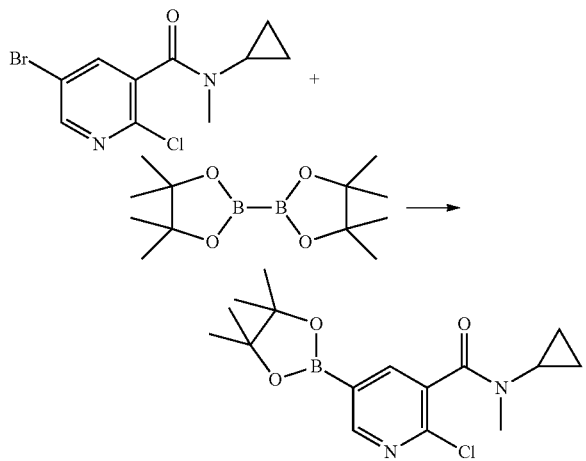

6.09 g (21.0 mmol) of 5-bromo-2-chloro-N-cyclopropyl-N-methylnicotinamide in 82 ml of dioxane were initially charged in a 250 ml flask and 5.88 g (23.1 mmol) of bispinacolatodiboron, 8.26 g (84.1 mmol) of anhydrous potassium acetate and 1.15 g (1.41 mmol) of ([1,1'-bis(diphenylphosphino)ferrocene]dichloropalladium(II) dichloromethane complex were added and the mixture heated to 80° C. for 4 hours under argon. The mixture was then cooled, filtered through kieselguhr and the filter cake washed with ethyl acetate. The filtrate was concentrated on a rotary evaporator under reduced pressure.

The residue was then taken up in methyl t-butyl ether and 10% aqueous sodium hydroxide solution was added. Undissolved constituents were filtered off and the phases then separated. The organic phase was post-extracted once with 10% aqueous sodium hydroxide solution. The combined aqueous phases were washed with methyl t-butyl ether, then acidified with cooling with concentrated aqueous hydrochloric acid and extracted three times with ethyl acetate. The combined organic phases were washed with saturated aqueous sodium chloride solution, dried with sodium sulphate and concentrated on a rotary evaporator under reduced pressure. 6.96 g of 2-chloro-N-cyclopropyl-N-methyl-5-(4,4,5,5-tetramethyl-1,3,2-dioxaborolan-2-yl)nicotinamide were obtained.

GC-MS[c]: Index=2380, mass (m/z)=336 [M]+.
$^1$H-NMR (400 MHz, d$_6$-DMSO): δ=8.62 (s, 1H), 7.99 (s, 1H), 6.98 (s, broad, 1H), 2.78-2.88 (m, 1H), 1.33 (s, 12H), 0.75-0.77 (m, 2H), 0.58-0.59 (m, 2H).

Preparation of [6-chloro-5-(cyclopropylcarbamoyl)pyridin-3-yl]boronic Acid (Compound of the Formula (i)) with Tetrahydroxydiboron

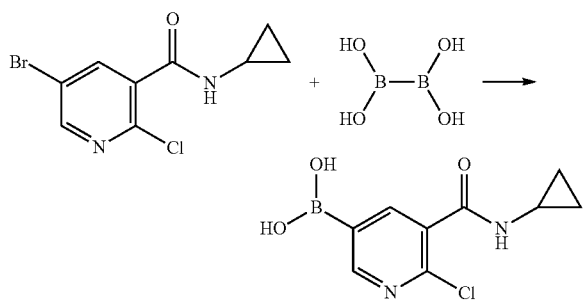

20 g (72.5 mmol) of 5-bromo-2-chloro-N-cyclopropylnicotinamide, 13.0 g (145 mmol) of tetrahydroxydiboron, 2.4 g (3.59 mmol) of cataCXium® A Pd G2 and 300 ml of methanol degassed with argon were initially charged in a 1000 ml flask under argon and then 38 ml (217 mmol) of diisopropylethylamine DIPEA were added and the mixture heated to 50° C. for 90 minutes. The mixture was then cooled and evaporated under reduced pressure on a rotary evaporator. The residue was partitioned between 146 ml of 10% aqueous NaOH and 146 ml of methyl t-butyl ether. Undissolved solid was filtered off and the residue on the filter washed with 60 ml of 10% aqueous NaOH and 60 ml of methyl t-butyl ether. The phases were then separated and the aqueous phase re-extracted with 100 ml of methyl t-butyl ether. The combined organic phases were re-extracted with 60 ml of 10% aqueous sodium hydroxide solution. With ice bath cooling at 0-10° C., the combined aqueous phases were adjusted to pH 1 by adding concentrated aqueous hydrochloric acid and the mixture was stirred for 5 minutes. The mixture was then extracted four times with ethyl acetate and the combined EE phases were dried with sodium sulphate and concentrated on a rotary evaporator under reduced pressure. 9.59 g of [6-chloro-5-(cyclopropylcarbamoyl)pyridin-3-yl]boronic acid remained as residue Content: 90% (quantitative NMR, compared to 99.8% 1,3,5-trimethoxybenzene)
HPLC-MS[a]: log P=0.44, mass (m/z)=241 [M+H]+.
$^1$H-NMR (400 MHz, d$_6$-DMSO): δ=8.69 (s, 1H), 8.10 (s, 1H), 6.5 (s, broad, 1H), 2.80-2.85 (m, 1H), 0.67-0.73 (m, 2H), 0.51-0.55 (m, 2H).

Prepared analogously were:

{6-Chloro-5-[(1-cyanocyclopropyl)carbamoyl]pyridin-3-yl}boronic Acid

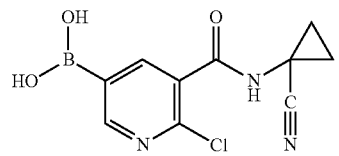 [SMILES: N#CC1(NC(=O)c2cc(B(O)O)cnc2Cl)CC1]

HPLC-MS[a]: log P=0.43, mass (m/z)=266 [M+H]+.
$^1$H-NMR (400 MHz, CD3CN): δ=8.72 (s, 1H), 8.14 (s, 1H), 7.68 (s, broad, 1H), 6.5 (s, broad, 2H), 1.55-1.58 (m, 1H), 1.30-1.38 (m, 1H).

{6-Chloro-5-[cyclopropyl(methyl)carbamoyl]pyridin-3-yl}boronic Acid

HPLC-MS[a]: log P=0.90, mass (m/z)=255 [M+H]+.
$^1$H-NMR (400 MHz, d$_6$-DMSO): The spectrum shows a mixture of rotamers in a ratio of ca. 16:84. δ=8.69 (s, 1H), 8.55 (s, broad, 2H), 8.11 (s, 0.84/1H), 8.05 (s, 0.16/1H), 3.00 (s, broad, 3H), 2.84-2.92 (m, 0.16/1H), 2.66-2.73 (m, 0.84/1H), 0.70-0.83 (m, 0.16/4H), 0.40-0.60 (m, 0.84/4H).

Preparation of Pyrazoles According to Formula (d)

1-[2-Chloro-4-[1,2,2,2-tetrafluoro-1-(trifluoromethyl)ethyl]-6-(trifluoromethoxy)phenyl]pyrazole 215.0 g (77.1% purity, 0.436 mol, 1.0 eq.) of 2-chloro-4-[1,2,2,2-tetrafluoro-1-(trifluoromethyl)ethyl]-6-(trifluoromethoxy)aniline were initially charged in 1250 g of glacial acetic acid at 22° C. To the solution was added with stirring a solution of 33.6 g (0.480 mol, 1.1 eq.) of sodium nitrite in 588.8 g of concentrated sulfuric acid over 30 minutes such that the reaction mixture warmed to 40° C. The mixture was then stirred at 40° C. for a further 30 minutes. A complete conversion of the starting material was observed. The solution was then cooled to 13° C. and a solution of 241.3 g (1.048 mmol, 2.4 eq.) of tin(II) chloride in 180.0 g of concentrated hydrochloric acid was added at 13-18° C. over 30 minutes with cooling in an ice bath. After the addition had ended, complete conversion to the hydrazine intermediate could be observed. The resulting reaction mixture was heated to 40° C. and 80.48 g (0.480 mol, 1.1 eq.) of 1,1,3,3-tetramethoxypropane were added in one portion. The mixture was then stirred at 40° C. for another 5 hours. A complete conversion to the product was observed. The mixture was tipped onto 1600 mL of deionized water/ice 1:1 (v/v) and the product was extracted into 1000 mL of isopropyl acetate/n-heptane 1:1 (v/v). After phase separation, the aqueous phase was re-extracted with 280 mL of isopropyl acetate/n-heptane 1:1 (v/v) and the combined organic phases were washed with 1×550 mL of 10% aqueous hydrochloric acid and 2×250 ml of saturated sodium chloride solution. After drying over 35 g of magnesium sulfate, filtration of the drying agent and removal of the solvent under reduced pressure, a dark red oil was obtained. The oil was subsequently subjected to vacuum distillation in a split-tube column. The product, a yellow oil, was collected at 0.05 mbar and 65° C.: yield 145.7 g (74% of theory at 95% purity) $^1$H-NMR (CDCl$_3$, 400 MHz) δ (ppm)=7.84 (s, 1H), 7.76 (s, 1H), 7.62 (s, 1H), 7.59 (s, 1H), 6.55 (s, 1H).

1-[2-Bromo-4-[1,2,2,2-tetrafluoro-1-(trifluoromethyl)ethyl]-6-(trifluoromethoxy)phenyl]pyrazole 352.0 g (89.4% purity, 0.742 mol, 1.0 eq.) of 2-bromo-4-[1,2,2,2-tetrafluoro-1-(trifluoromethyl)ethyl]-6-(trifluoromethoxy)aniline were initially charged in 2098 g of glacial acetic acid at 22° C. To the solution was added with stirring a solution of 56.3 g (0.816 mol, 1.1 eq.) of sodium nitrite in 991.6 g of concentrated sulfuric acid over 1 hour 10 minutes such that the reaction mixture warmed to 40° C. The mixture was then stirred at 40° C. for a further 10 minutes. A complete conversion of the starting material was observed. The solution was then cooled to 15° C. and a solution of 401.9 g (1.781 mmol, 2.4 eq.) of tin(II) chloride in 242.0 mL of concentrated hydrochloric acid was added at 15-20° C. over 1 hour 15 minutes with external cooling at 10° C. After addition was complete and further stirring for 10 minutes at 20° C., complete conversion to the hydrazine intermediate could be observed. The resulting reaction mixture was heated to 40° C. and 134.0 g (0.816 mol, 1.1 eq.) of 1,1,3,3-tetramethoxypropane were added over 10 minutes. The mixture was then stirred at 40° C. for another 5 hours. A complete conversion to the product was observed. The mixture was tipped onto 2640 mL of deionized water/ice 1:1 (v/v) and the product was extracted into 1760 mL of isopropyl acetate/n-heptane 1:1 (v/v). After phase separation, the aqueous phase was re-extracted with 440 mL of isopropyl acetate/n-heptane 1:1 (v/v) and the combined organic phases were washed with 1×880 mL of 10% aqueous hydrochloric acid and 2×440 ml of saturated sodium chloride solution. After drying over 60 g of magnesium sulfate, filtration of the drying agent and removal of the solvent under reduced pressure, a dark red oil was obtained. The oil was subsequently subjected to vacuum distillation in a split-tube column. The product, an orange oil, was collected at 0.05 mbar and 70° C.: yield 245.1 g (68% of theory at 97.5% purity) $^1$H-NMR (CDCl$_3$, 600 MHz) δ (ppm)=7.93 (s, 1H), 7.84 (s, 1H), 7.63 (s, 1H), 7.61 (s, 1H), 6.55 (s, 1H).

The following compounds were obtained analogously:

1-[4-(1,1,1,2,3,3,3-heptafluoropropan-2-yl)-2,6-dimethylphenyl]-1H-pyrazole

HPLC-MS$^{a)}$: log P=4.30, mass (m/z)=341 [M+H]+.
$^1$H-NMR (400 MHz, d$_3$-acetonitrile): δ=7.3 (d, J=1.5 Hz, 1H), 7.3 (d, J=2 Hz, 1H), 7.51 (s, 2H), 6.52 (m, 2H), 2.04 (s, 6H).

1-[2,6-dichloro-4-(1,1,1,2,3,3,3-heptafluoropropan-2-yl)phenyl]-1H-pyrazole

HPLC-MS$^{a)}$: log P=4.22, mass (m/z)=381 [M+H]+.
$^1$H-NMR (400 MHz, d$_3$-acetonitrile): δ=7.87 (s, 2H), 7.80 (d, J=1.4 Hz, 1H), 7.76 (m, 1H), 6.56-6.57 (m, 1H).

1-[2-chloro-4-(1,1,1,2,3,3,3-heptafluoropropan-2-yl)-6-(trifluoromethyl)phenyl]-1H-pyrazole HPLC-MS$^{a)}$: log P=4.38, mass (m/z)=415 [M+H]+.
$^1$H-NMR (400 MHz, d$_3$-acetonitrile): δ=8.18 (s, 1H), 8.03 (s, 1H), 7.79 (d, J=1.6 Hz, 1H), 7.77 (d, J=1.6 Hz, 1H), 6.56-6.57 (m, 1H).

1-[2-chloro-6-(difluoromethoxy)-4-(1,1,1,2,3,3,3-heptafluoropropan-2-yl)phenyl]-1H-pyrazole HPLC-MS$^{a)}$: log P=4.04, mass (m/z)=413 [M+H]+.
$^1$H-NMR (400 MHz, d$_6$-DMSO): δ=8.08 (d, J=2.4 Hz, 1H), 7.92 (s, 1H), 7.83 (d, J=1.6 Hz, 1H), 7.64 (s, 1H), 7.35 (t, J=72 Hz, 1H), 6.56-6.57 (m, 1H).

1-[4-(1,1,1,2,3,3,3-heptafluoropropan-2-yl)-2-methyl-6-(trifluoromethyl)phenyl]-1H-pyrazole HPLC-MS$^{a)}$: log P=4.4, mass (m/z)=395 [M+H]+.
$^1$H-NMR (400 MHz, d$_3$-acetonitrile): δ=7.96 (s, 1H), 7.92 (s, 1H), 7.76 (d, J=1.6 Hz, 1H), 7.72 (d, J=2.2 Hz, 1H), 6.53-6.54 (m, 1H), 2.03 (s, 3H).

1-[2-bromo-4-(1,1,1,2,3,3,3-heptafluoropropan-2-yl)-6-(trifluoromethyl)phenyl]-1H-pyrazole HPLC-MS$^{a)}$: log P=4.42, mass (m/z)=459 [M+H]+.
$^1$H-NMR (400 MHz, d$_3$-acetonitrile): δ=8.31 (s, 1H), 8.06 (s, 1H), 7.78 (s, 1H), 7.75 (s, 1H), 6.56 (s, 1H). The N-arylpyrazoles obtained can be halogenated with high selectivity in the 4-position of the pyrazole.

Preparation of Halogen-Substituted Pyrazoles According to Formula (f)

The following examples describe the bromination and iodination of 1-[2-chloro-4-[1,2,2,2-tetrafluoro-1-(trifluoromethyl)ethyl]-6-(trifluoromethoxy)phenyl]pyrazole and the iodination of 1-[2-bromo-4-[1,2,2,2-tetrafluoro-1-(trifluoromethyl)ethyl]-6-(trifluoromethoxy)phenyl]pyrazole:

4-Bromo-1-[2-chloro-4-[1,2,2,2-tetrafluoro-1-(trifluoromethyl)ethyl]-6-(trifluoromethoxy)phenyl]pyrazole 5.0 g (98.0% purity, 11.38 mmol, 1.00 eq.) of 1-[2-chloro-4-[1,2,2,2-tetrafluoro-1-(trifluoromethyl)ethyl]-6-(trifluoromethoxy)phenyl]pyrazole were initially charged in 10.0 g of acetonitrile at 22° C. To the solution was added with stirring 1.79 g (28.45 mol, 0.55 eq.) of 1,3-dibromo-5,5-dimethylhydantoin in one portion. The resulting suspension was then heated to 82° C. A complete conversion to the product was observed after stirring for a further 3 hours. The mixture was subsequently tipped onto 100 mL of semi-concentrated sodium chloride solution and the product was extracted into 100 mL of n-heptane. The organic phase was washed with 2×50 mL of 10% aqueous sodium hydroxide solution and 1× with 50 mL of 10% aqueous sodium thiosulfate solution, dried over 1 g of magnesium sulfate, the drying agent removed by filtration and the solvent removed under reduced pressure. A black oil was obtained: yield 5.50 g (91% of theory at 96.4% purity)$^1$H-NMR (CDCl$_3$, 400 MHz) δ (ppm)=7.79 (s, 1H), 7.76 (s, 1H), 7.64 (s, 1H), 7.59 (s, 1H).

The following compound was obtained analogously:

4-bromo-1-[2,6-dichloro-4-(1,1,1,2,3,3,3-heptafluoropropan-2-yl)phenyl]-1H-pyrazole HPLC-MSa): log P=5.07, mass (m/z)=459 [M+H]+.
1H-NMR (400 MHz, d3-acetonitrile): δ=7.89 (m, 3H), 7.83 (s, 1H).

1-[2-chloro-4-(1,1,1,2,3,3,3-heptafluoropropan-2-yl)-6-(trifluoromethoxy)phenyl]-4-iodo-1H-pyrazole 5.0 g (98.0% purity, 11.38 mmol, 1.0 eq.) of 1-[2-chloro-4-[1,2,2,2-tetrafluoro-1-(trifluoromethyl)ethyl]-6-(trifluoromethoxy)phenyl]pyrazole were initially charged in 10.0 g of acetonitrile at 22° C. To the solution was added with stirring 6.4 g (28.45 mol, 2.5 eq.) of N-iodosuccinimide in one portion. The resulting suspension was then heated to 82° C. A complete conversion to the product was observed after stirring for a further 1 hour. The mixture was subsequently tipped onto 100 mL of semi-concentrated sodium chloride solution and the product was extracted into 100 mL of n-heptane. The organic phase was washed with 2×50 mL of 10% aqueous sodium hydroxide solution and 1× with 50 mL of 10% aqueous sodium thiosulfate solution, dried over 1 g of magnesium sulfate, the drying agent removed by filtration and the solvent removed under reduced pressure. A pale brown oil was obtained: yield 6.06 g (96% of theory at 99.9% purity)$^1$H-NMR (CDCl$_3$, 400 MHz) δ (ppm)=7.83 (s, 1H), 7.76 (s, 1H), 7.66 (s, 1H), 7.59 (s, 1H).

4-Iodo-1-[2-bromo-4-[1,2,2,2-tetrafluoro-1-(trifluoromethyl)ethyl]-6-(trifluoromethoxy)phenyl]pyrazole 391.7 g (96.6% purity, 0.796 mol, 1.0 eq.) of 1-[2-bromo-4-[1,2,2,2-tetrafluoromethyl)ethyl]-6-(trifluoromethoxy)phenyl]pyrazole were initially charged in 751.1 g of acetonitrile at 22° C. To the solution was added with stirring 277.1 g (1.194 mol, 1.5 eq.) of N-iodosuccinimide in one portion. The resulting suspension was then heated to 82° C. A complete conversion to the product was observed after stirring for a further 8 hours. 391.3 g of acetonitrile were distilled off from the mixture. The residue was then taken up in 1500 mL of n-heptane and the organic phase was washed with 1×3000 mL of 10% aqueous sodium hydroxide solution, then with 1×1500 mL of 10% aqueous sodium hydroxide solution and subsequently with 1×500 mL of sodium chloride solution. The organic phase was then dried over 50 g of magnesium sulfate, the drying agent removed by filtration and the solvent removed under reduced pressure. 487.7 g (99% of theory at 97.1% purity) of solid were obtained.

$^1$H-NMR (CDCl$_3$, 600 MHz) δ (ppm)=7.92 (s, 1H), 7.83 (s, 1H), 7.65 (s, 1H), 7.63 (s, 1H).

The following iodopyrazoles were obtained analogously:

1-[4-(1,1,1,2,3,3,3-heptafluoropropan-2-yl)-2,6-dimethylphenyl]-4-iodo-1H-pyrazole HPLC-MSa): log P=5.2, mass (m/z)=467 [M+H]+.
1H-NMR (400 MHz, d3-acetonitrile): δ=7.80 (s, 1H), 7.79 (s, 1H), 7.5 (s, 2H), 2.05 (s, 6H).

1-[2,6-dichloro-4-(1,1,1,2,3,3,3-heptafluoropropan-2-yl)phenyl]-4-iodo-1H-pyrazole HPLC-MSa): log P=5.17, mass (m/z)=507 [M+H]+.
1H-NMR (400 MHz, d3-acetonitrile): δ=7.88 (m, 3H), 7.86 (s, 1H).

1-[2-chloro-4-(1,1,1,2,3,3,3-heptafluoropropan-2-yl)-6-(trifluoromethyl)phenyl]-4-iodo-1H-pyrazole HPLC-MSa): log P=5.19, mass (m/z)=541 [M+H]+.
1H-NMR (400 MHz, d3-acetonitrile): δ=8.19 (s, 1H), 8.03 (s, 1H), 7.89 (s, 1H), 7.85 (s, 1H).

1-[2-bromo-4-(1,1,1,2,3,3,3-heptafluoropropan-2-yl)-6-(trifluoromethyl)phenyl]-4-iodo-1H-pyrazole HPLC-MSa): log P=5.22, mass (m/z)=585 [M+H]+.
1H-NMR (400 MHz, d3-acetonitrile): δ=8.32 (s, 1H), 8.07 (s, 1H), 7.88 (s, 1H), 7.85 (s, 1H).

1-[2-chloro-6-(difluoromethoxy)-4-(1,1,1,2,3,3,3-heptafluoropropan-2-yl)phenyl]-4-iodo-1H-pyrazole HPLC-MSa): log P=4.82, mass (m/z)=539 [M+H]+.
1H-NMR (400 MHz, d3-acetonitrile): δ=7.88 (s, 1H), 7.84 (s, 1H), 7.81 (s, 1H), 7.55 (s, 1H), 6.78 (t, J=72 Hz, 1H).

Preparation of Compounds of the Formula (h)

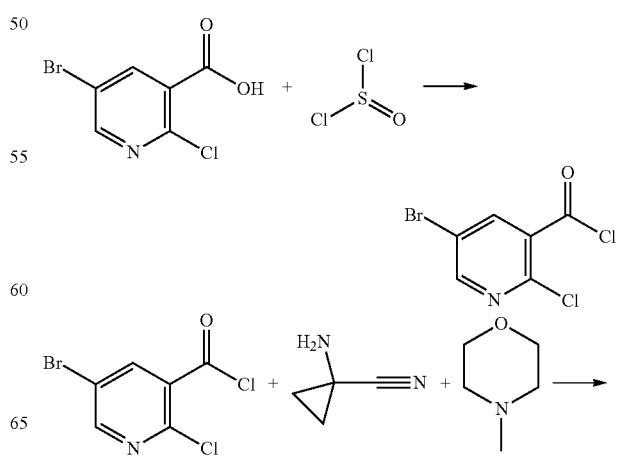

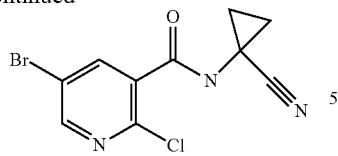

69 ml of toluene were initially charged in a 250 ml flask, 232 mg (3.17 mmol) of dimethylformamide were added and then 15 g (63.4 mmol) of 2-chloro-5-bromonicotinic acid were introduced. Subsequently, 22.64 g (190 mmol) of thionyl chloride were then added dropwise. The suspension was then heated slowly to 100-105° C. with evolution of gas. A solution was formed which was kept at 100-105° C. for one hour. The mixture was then cooled and the excess thionyl chloride and the solvent were removed under reduced pressure on a rotary evaporator. The residue was dissolved in 38 ml of chloroform and slowly added dropwise with cooling to a dilute suspension of 150 ml of chloroform, 15.04 g (126 mmol) of 1-cyanocyclopropylamine hydrochloride and 25.67 g (253 mmol) of N-methylmorpholine. The mixture was then stirred at room temperature overnight. For the work-up, the mixture was poured onto saturated aqueous sodium hydrogencarbonate solution, the organic phase separated with the solid suspended therein, the organic phase washed once with water and the solid then filtered off with suction and dried in air. 18.3 g of 5-bromo-2-chloro-N-(1-cyancyclopropyl)nicotinamide were obtained.

HPLC-MS[a)]: log P=1.45, mass (m/z)=300 [M+H]$^+$.

$^1$H-NMR (400 MHz, d$_3$-acetonitrile): δ=8.56 (s, 1H), 8.05 (s, 1H), 7.72 (s, broad, 1H), 1.52-1.63 (m, 1H), 1.27-1.39 (m, 1H).

Synthesis of the End Products

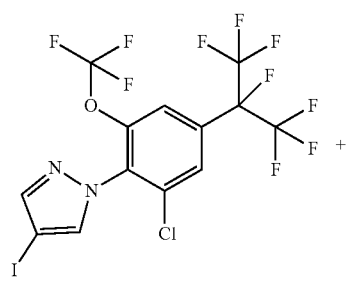

MW = 556.53
EM = 555.89
C13H4ClF10IN2O

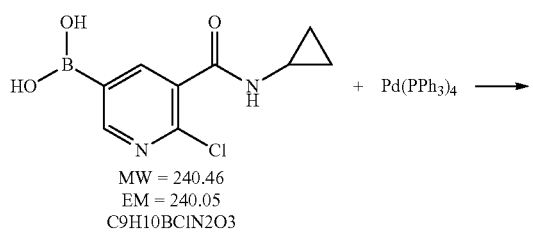

MW = 240.46
EM = 240.05
C9H10BClN2O3

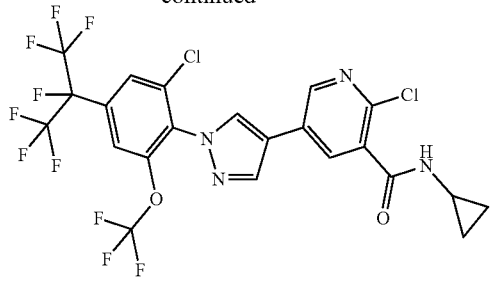

MW = 625.26
EM = 624.02
C22H12Cl2F10N4O2

22.45 g (91.7%, 37 mmol) of 1-[2-chloro-4-(1,1,1,2,3,3,3-heptafluoropropan-2-yl)-6-(trifluoromethoxy)phenyl]-4-iodo-1H-pyrazole and 13.3 g (76.9%, 42.5 mmol) of [6-chloro-5-(cyclopropylcarbamoyl)pyridin-3-yl]boronic acid in 923 ml of isopropanol were initially charged in a 2000 ml flask under argon. 113 ml (113 mmol) of degassed 1 molar aqueous potassium carbonate solution and 2.565 g (2.21 mmol) of tetrakis(triphenylphosphine)palladium(0) were then added. The mixture was heated to 65° C. under argon for 2.5 hours. The mixture was then cooled and the solvent removed under reduced pressure on a rotary evaporator. The residue was partitioned between water and ethyl acetate. The organic phase was separated off and the aqueous phase was once more extracted with ethyl acetate. The combined organic phases were then washed once with saturated aqueous sodium chloride solution and concentrated on a rotary evaporator under reduced pressure. The residue was purified in portions through a cartridge containing 340 g of silica gel using a cyclohexane/ethyl acetate gradient of 90:10 to 35:65 (v/v). 17.42 g (73% of theory) of 2-chloro-5-{1-[2-chloro-4-(1,1,1,2,3,3,3-heptafluoropropan-2-yl)-6-(trifluoromethoxy)phenyl]-1H-pyrazol-4-yl}-N-cyclopropylnicotinamide were obtained at a purity of 96.89% (LC/MS area).

HPLC-MS[a)]: log P=4.28, mass (m/z)=625 [M+H]$^+$.

$^1$H-NMR (400 MHz, d$_3$-acetonitrile): δ=8.70 (d, J=2.4 Hz, 1H), 8.25 (s, 1H), 8.24 (s, 1H), 8.05 (d, J=2.4 Hz, 1H), 7.96 (s, 1H), 7.76 (s, 1H), 7.04 (s (broad), 1H (N—H)), 2.82-2.89 (m, 1H), 0.74-0.81 (m, 2H), 0.54-0.65 (m, 2H).

Prepared analogously were:

2-Chloro-5-{1-[2-chloro-4-(1,1,1,2,3,3,3-heptafluoropropan-2-yl)-6-(trifluoromethyl)phenyl]-1H-pyrazol-4-yl}-N-cyclopropylnicotinamide HPLC-MS[a)]: log P=4.0, mass (m/z)=609 [M+H]$^+$.

$^1$H-NMR (400 MHz, d$_3$-acetonitrile): δ=8.70 (d, J=2.5 Hz, 1H), 8.24 (s, 1H), 8.23 (s, 2H), 8.06 (d, J=2.5 Hz, 1H), 7.04 (s (broad), 1H (N—H)), 2.82-2.88 (m, 1H), 0.74-0.81 (m, 2H), 0.54-0.65 (m, 2H).

2-Chloro-5-{1-[2-chloro-4-(1,1,1,2,3,3,3-heptafluoropropan-2-yl)-6-(trifluoromethoxy)phenyl]-1H-pyrazol-4-yl}-N-cyclopropyl-N-methylnicotinamide HPLC-MS[a)]: log P=4.56, mass (m/z)=639 [M+H]$^+$.

$^1$H-NMR (400 MHz, d$_3$-acetonitrile): δ=8.69 (d, J=2.4 Hz, 1H), 8.25 (s, 1H), 8.24 (s, 1H), 8.00 (d, J=2.4 Hz, 1H), 7.98 (s, 1H), 7.77 (s, 1H), 3.07 (s, 3H), 2.75-2.78 (m, 1H), 0.52-0.62 (m, 4H).

5-{1-[2-Bromo-4-(1,1,1,2,3,3,3-heptafluoropropan-2-yl)-6-(trifluoromethoxy)phenyl]-1H-pyrazol-4-yl}-2-chloro-N-cyclopropylnicotinamide HPLC-MS[a)]: log P=4.25, mass (m/z)=669 [M+H]+.
1H-NMR (400 MHz, d3-acetonitrile): δ=8.70 (d, J=2.4 Hz, 1H), 8.24 (s, 2H), 8.11 (s, 1H), 8.04 (d, J=2.4 Hz, 1H), 7.80 (s, 1H), 7.01 (s (broad), 1H (N—H)), 2.83-2.89 (m, 1H), 0.76-0.81 (m, 2H), 0.54-0.62 (m, 2H).

2-Chloro-5-{1-[2-chloro-4-(1,1,1,2,3,3,3-heptafluoropropan-2-yl)-6-(trifluoromethyl)phenyl]-1H-pyrazol-4-yl}-N-cyclopropyl-N-methylnicotinamide HPLC-MS[a)]: log P=4.46, mass (m/z)=623 [M+H]+.
1H-NMR (400 MHz, d6-DMSO): δ=8.83 (s, 1H), 8.81 (d, J=2.4 Hz, 1H), 8.54 (s, 1H), 8.51 (s, 1H), 8.32 (d, J=2.4 Hz, 1H), 8.10 (s, 1H), 3.90 (s, 3H), 2.76-2.81 (m, 1H), 0.52-0.62 (m, 4H).

2-Chloro-N-(1-cyanocyclopropyl)-5-{1-[2,6-dichloro-4-(1,1,1,2,3,3,3-heptafluoropropan-2-yl)phenyl]-1H-pyrazol-4-yl}nicotinamide HPLC-MS[a)]: log P=3.81, mass (m/z)=600 [M+H]+.
1H-NMR (400 MHz, d6-DMSO): δ=9.60 (s, 1H), 8.87 (d, J=2.4 Hz, 1H), 8.84 (s, 1H), 8.55 (s, 1H), 8.28 (d, J=2.4 Hz, 1H), 8.11 (s, 2H), 1.61-1.64 (m, 2H), 1.24-1.30 (m, 2H).

2-Chloro-N-(1-cyanocyclopropyl)-5-{1-[4-(1,1,1,2,3,3,3-heptafluoropropan-2-yl)-2,6-dimethylphenyl]-1H-pyrazol-4-yl}nicotinamide HPLC-MS[a)]: log P=3.87, mass (m/z)=560 [M+H]+.
1H-NMR (600 MHz, d6-DMSO): δ=9.59 (s, 1H), 8.86 (d, J=2.4 Hz, 1H), 8.71 (s, 1H), 8.46 (s, 1H), 8.26 (d, J=2.4 Hz, 1H), 7.60 (s, 2H), 2.12 (s, 6H), 1.61-1.64 (m, 2H), 1.26-1.29 (m, 2H).

2-Chloro-N-cyclopropyl-5-{1-[2,6-dichloro-4-(1,1,1,2,3,3,3-heptafluoropropan-2-yl)phenyl]-1H-pyrazol-4-yl}-N-methylnicotinamide HPLC-MS[a)]: log P=4.36, mass (m/z)=589 [M+H]+.
1H-NMR (400 MHz, d6-DMSO): δ=8.83 (s, 1H), 8.81 (d, J=2.4 Hz, 1H), 8.53 (s, 1H), 8.32 (d, J=2.4 Hz, 1H), 8.11 (s, 1H), 2.76-3.00 (m, 1H), 0.51-0.60 (m, 4H).

5-{1-[2-Bromo-4-(1,1,1,2,3,3,3-heptafluoropropan-2-yl)-6-(trifluoromethoxy)phenyl]-1H-pyrazol-4-yl}-2-chloro-N-cyclopropyl-N-methylnicotinamide

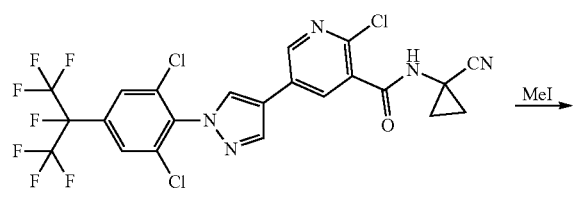

MW = 600.7
EM = 598.99
C22H11Cl3F7N5O

MeI→

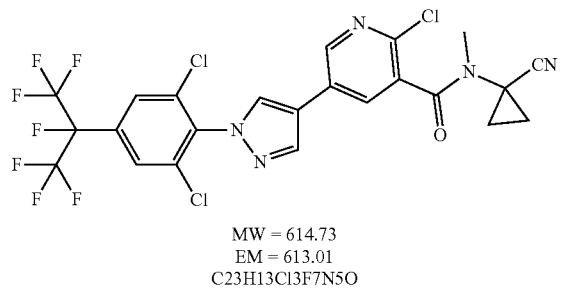

MW = 614.73
EM = 613.01
C23H13Cl3F7N5O 1.58 g (2.69 mmol) of 1-[2-bromo-4-(1,1,1,2,3,3,3-heptafluoropropan-2-yl)-6-(trifluoromethyl)phenyl]-4-iodo-1H-pyrazol and 1.39 g (content 75%, 3.1 mmol) of 2-chloro-N-cyclopropyl-N-methyl-5-(4,4,5,5-tetramethyl-1,3,2-dioxaborolan-2-yl)nicotinamide in 69 ml of isopropanol were initially charged in a 250 ml flask under argon. Next, 8.2 ml (8.2 mmol) of 1 molar aqueous potassium carbonate solution degassed with argon and 0.187 g (0.16 mmol) of tetrakis(triphenylphosphine)palladium(0) were then added. The mixture was then stirred overnight at 60° C. For the workup, the mixture was then cooled and evaporated under reduced pressure on a rotary evaporator. The residue was partitioned between water and dichloromethane. The organic phase was removed and the aqueous phase was re-extracted twice with dichloromethane. The combined organic phases were then washed once with 10% aqueous sodium hydroxide solution and then with saturated aqueous sodium chloride solution, dried with sodium sulphate and concentrated on a rotary evaporator under reduced pressure. The residue was purified by chromatography through a cartridge containing 40 g of silica gel with a gradient of cyclohexane/ethyl acetate of 95:5 to 65:35 (v/v). 1.0 g of 5-{1-[2-bromo-4-(1,1,1,2,3,3,3-heptafluoropropan-2-yl)-6-(trifluoromethyl)phenyl]-1H-pyrazol-4-yl}-2-chloro-N-cyclopropyl-N-methylnicotinamide was obtained.

HPLC-MS[a)]: log P=4.28, mass (m/z)=667 [M+H]+.
1H-NMR (400 MHz, d3-acetonitrile): δ=8.69 (d, J=2.4 Hz, 1H), 8.35 (s, 1H), 8.22 (s, 1H), 8.21 (s, 1H), 8.10 (s, 1H), 8.00 (d, J=2.4 Hz, 1H), 3.07 (s, 3H), 2.74-2.81 (m, 1H), 0.54-0.62 (m, 4H).

2-Chloro-N-(1-cyanocyclopropyl)-5-{1-[2,6-dichloro-4-(1,1,1,2,3,3,3-heptafluoropropan-2-yl)phenyl]-1H-pyrazol-4-yl}-N-methylnicotinamide

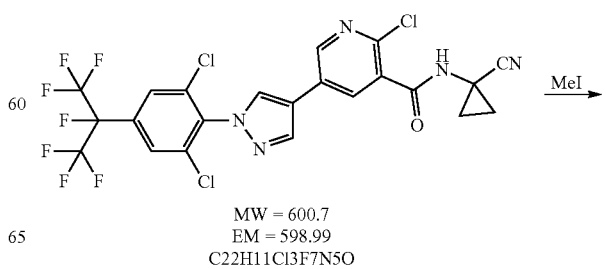

MW = 600.7
EM = 598.99
C22H11Cl3F7N5O

MeI→

-continued

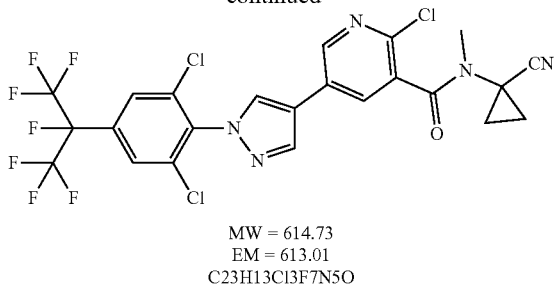

MW = 614.73
EM = 613.01
C23H13Cl3F7N5O

To a solution of 404 mg (0.673 mmol) of 2-chloro-N-(1-cyanocyclopropyl)-5-{1-[2,6-dichloro-4-(1,1,1,2,3,3,3-heptafluoropropan-2-yl)phenyl]-1H-pyrazol-4-yl}nicotinamide in 10 mL of THF at 0° C. was added 38 mg (0.88 mmol) of a 55 percent dispersion of sodium hydride in mineral oil and the reaction mixture was stirred at 0° C. for 10 min. Subsequently, 0.05 mL (0.9 mmol) of methyl iodide was added and the reaction mixture was stirred at room temperature overnight. 2 mL of ethyl acetate were added and the solvent was subsequently removed under reduced pressure. The residue was dissolved in $CH_2Cl_2$ and washed with water. The organic phase was dried over sodium sulfate and filtered, and the solvent was removed under reduced pressure. The residue was purified chromatographically by MPLC on reversed-phase silica gel (gradient: water/acetonitrile 70:30-0:100). 327 mg of 2-chloro-N-(1-cyanocyclopropyl)-5-{1-[2,6-dichloro-4-(1,1,1,2,3,3,3-heptafluoropropan-2-yl)phenyl]-1H-pyrazol-4-yl}-N-methylnicotinamide were obtained.

HPLC-MS[a]: log P=4.31, mass (m/z)=614 [M+H]$^+$.

$^1$H-NMR (400 MHz, $CDCl_3$): The spectrum shows a mixture of rotamers in a ratio of ca. 44:56. δ=8.71 (d, J=1.8 Hz, 0.44/1 H), 8.68 (d, J=1.9 Hz, 0.56/1 H), 8.20 (s, 0.44/1 H), 8.16 (s, 0.56/1 H), 8.08 (d, J=1.9 Hz, 0.44/1 H), 7.99 (s, 0.44/1 H), 7.96 (s, 0.56/1 H), 7.91 (d, J=2.1 Hz, 0.56/1H), 7.56 (s, 1.12/2 H), 7.74 (s, 0.88/2 H), 3.26 (s, 1.32/3 H), 3.03 (s, 1.68/3 H), 1.10-1.90 (m (broad), 4H).

[a]) Note regarding the determination of the log P values and mass detection: The determination of the given log P values was carried out in accordance with EEC Directive 79/831 Annex V.A8 by HPLC (High Performance Liquid Chromatography) on a reversed-phase column (C18). Agilent 1100 LC system; 50*4.6 Zorbax Eclipse Plus C18 1.8 micron; mobile phase A: acetonitrile (0.1% formic acid); mobile phase B: water (0.09% formic acid); linear gradient from 10% acetonitrile to 95% acetonitrile in 4.25 min, then 95% acetonitrile for a further 1.25 min; oven temperature 55° C.; flow rate: 2.0 ml/min. Mass detection is via an Agilent MSD system. The mass stated is the peak of the molecular ion+hydrogen [M+H]$^+$ (molecular ion=sum of the masses of the most abundant natural isotopes of which the molecule consists).

[b]) HPLC (High Performance Liquid Chromatography) on a reversed-phase column (C18), Agilent 1100 LC system; 50*4.6 Zorbax XDB C18 1.8 micron; mobile phase A: acetonitrile; mobile phase B: water (79 mg of ammonium bicarbonate/l); linear gradient from 10% acetonitrile to 95% acetonitrile in 4.25 min, then 95% acetonitrile for a further 1.55 min; oven temperature 55° C.; flow rate: 2.0 ml/min. Mass detection is via an Agilent MSD system. The mass stated is the peak of the molecular ion+hydrogen [M+H]$^+$ (molecular ion=sum of the masses of the most abundant natural isotopes of which the molecule consists).

[c]) GC/MS (gas chromatography/mass spectrometry) on dimethylsilicone phase. 10 m DB-1, ID=0.18 mm, film thickness=0.4 μm; injector: 250° C., carrier gas flow rate: 1.6 mm/min helium; detector: MSD: 280° C., FID: 320° C.; oven temperature: 50° C. (1 minute), 50° C.-320° C. (3.25 minutes), 40° C./min), 320° C. (6.75 minutes); Kovacs Indices calibrated with alkane mixture.

The invention claimed is:

1. A Method for preparing one or more compounds of formula (I)

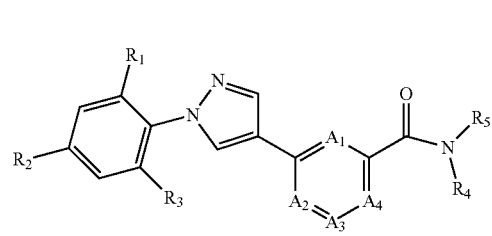

(I)

where
$R_1$ is halogen, $C_1$-$C_4$-alkyl optionally substituted by halogen or CN or $C_1$-$C_4$-alkoxy optionally substituted by halogen;
$R_2$ is halogen, $C_1$-$C_4$-alkyl optionally substituted by halogen or $C_1$-$C_4$-alkoxy optionally substituted by halogen;
$R_3$ is halogen, $C_1$-$C_4$-alkyl optionally substituted by halogen or CN or $C_1$-$C_4$-alkoxy optionally substituted by halogen;
$R_4$ is hydrogen, $C_1$-$C_4$-alkyl optionally substituted by halogen or CN or $C_3$-$C_6$-cycloalkyl optionally substituted by halogen or CN;
$R_5$ is hydrogen, $C_1$-$C_4$-alkyl optionally substituted by halogen or CN or $C_3$-$C_6$-cycloalkyl optionally substituted by halogen or CN;
$A_1$ is =C($R_6$)-;
$A_2$ is =C($R_7$)-;
$A_3$ is N;
$A_4$ is =C($R_9$)-;
$R_6$, $R_7$, and $R_9$ are each independently hydrogen, $C_1$-$C_4$-alkyl optionally substituted by halogen or CN, or halogen,
said method comprising:
a) reacting one or more compounds of formula (a) to give one or more compounds of formula (d) in a one-pot reaction comprising diazotization of the compound of the formula (a) (reaction 1), reduction of the resulting salt to give a hydrazine compound of the formula (b) (reaction 2) and cyclization of the resulting compound to give compound (d) (reaction 3)

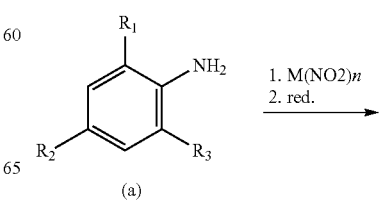

(a)

-continued

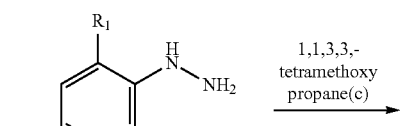

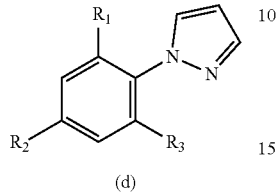

wherein in step a), the M(NO$_2$)$_n$, in reaction 1 is LiNO$_2$, NaNO$_2$, KNO$_2$, Mg(NO$_2$)$_2$, Ca(NO$_2$)$_2$ or Ba(NO$_2$)$_2$, and reaction 2 comprises adding a reducing agent to reaction mixture comprising resulting diazonium salt derived from reaction 1 to obtain reduction of the resulting diazonium salt to give the hydrazine compound of the formula (b), wherein the reducing agent is tin(II) salt or sulphite, b) reacting a compound of formula (d) with a halogenating compound to give a compound of formula (f)

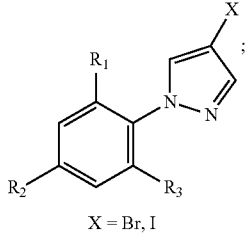

c) reacting a compound of formula (f) with a compound of formula (i) to give a compound of formula (I)

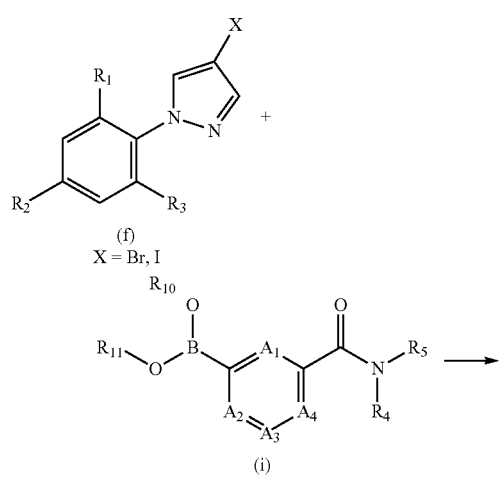

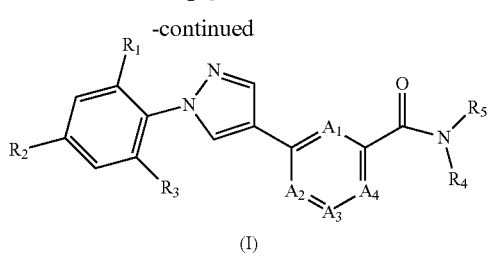

where R$_{10}$ and R$_{11}$ are each independently H or C$_1$-C$_6$-alkyl or R$_{10}$ and R$_{11}$ are together a C$_1$-C$_8$-alkyl bridge, wherein conversion of a compound of formula (a) to a compound of formula (d) meets the following conditions:
i) there is no isolation of diazonium ion (diazonium salt) from the reaction mixture of reaction 1;
ii) there is no purification of diazonium ion (diazonium salt) from the reaction mixture of reaction 1;
iii) there is no isolation of compound (b) from the reaction mixture of reaction 2;
iv) there is no purification of a compound (b) from the reaction mixture of reaction 2;
v) all reactions 1, 2 and 3 are carried out in the same reaction vessel;
vi) less than 50% by volume (percent by volume based on the volume of solvent used) of solvent from reaction 1 is removed prior to the start of the second reaction or prior to the start of reaction 3 (optionally by evaporation or active removal).

2. Method according to claim 1, wherein neither the diazonium ion (diazonium salt) formed from compound (a) nor compound (b) are isolated or purified during the reaction sequence which leads to compound (d).

3. Method according to claim 1, wherein neither the diazonium ion (diazonium salt) formed from compound (a) nor compound (b) are isolated or purified during the reaction sequence which leads to compound (d), nor is there an essential removal and/or exchange of solvent.

4. Method according claim 1, wherein the halogenating compound of step b) is bromine, iodine, an inorganic bromine or iodine salt or an organic bromine or iodine molecule in which the bond of an organic radical to the bromine is polarized such that the bromine or iodine is a carrier of a partial positive charge, optionally bromine, iodine, N-bromosuccinimide, N-iodosuccinimide, 1,3-dibromo-5-5-dimethylhydantoin or iodine monochloride.

5. Method according to claim 1, wherein the reaction of a compound of the formula (i) with a compound of the formula (f) in step c) is catalyzed by a palladium catalyst.

6. Method according to claim 5, wherein the reaction is catalyzed by tetrakis(triphenylphosphine)palladium(0), bis(triphenylphosphine)palladium(II) chloride or a mixture thereof.

7. Method according to claim 5, wherein the reaction of a compound of formula (i) with a compound of formula (f) in c) is carried out in the presence of at least one base, wherein the base is selected from a group consisting of sodium carbonate, potassium carbonate, caesium carbonate, sodium bicarbonate and potassium phosphate.

8. Method according to claim 1, wherein a compound of formula (i) is prepared by reacting a compound of formula (h)

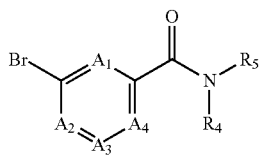

with a boron donor of formula

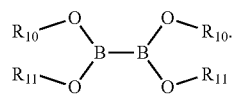

9. Method according to claim 1, wherein the one pot reaction in step a) is a telescoped reaction.

10. Method according to claim 1, wherein
(vi) less than 30% by volume (percent by volume based on the volume of solvent used) of solvent from reaction 1 is removed prior to the start of the second reaction or prior to the start of reaction 3 (optionally by evaporation or active removal), and no solvent is actively removed by solvent exchange between reaction 1 and reaction 2 and between reaction 2 and 3.

11. Method according to claim 1, wherein
(vi) less than 10% by volume (percent by volume based on the volume of solvent used) of solvent from reaction 1 is removed prior to the start of the second reaction or prior to the start of reaction 3 (optionally by evaporation or active removal), and no solvent is actively removed by solvent exchange between reaction 1 and reaction 2 and between reaction 2 and 3.

12. Method according to claim 1, wherein
(vi) at most 5% by volume (percent by volume based on the volume of solvent used) of solvent from reaction 1 is removed prior to the start of the second reaction or prior to the start of reaction 3 (optionally by evaporation or active removal), and no solvent is actively removed by solvent exchange between reaction 1 and reaction 2 and between reaction 2 and 3.

13. Method according to claim 1, wherein
vii) at most 40% by volume of the solvent used prior to reaction 1 is replaced by a new solvent, wherein the new solvent can be the same solvent or another solvent.

14. Method according to claim 1, wherein
vii) at most 30% by volume of the solvent used prior to reaction 1 is replaced by a new solvent, wherein the new solvent can be the same solvent or another solvent.

15. Method according to claim 1, wherein
vii) at most 20% by volume of the solvent used prior to reaction 1 is replaced by a new solvent, wherein the new solvent can be the same solvent or another solvent.

16. Method according to claim 1, wherein the reducing agent is a tin(II) salt.

17. Method according to claim 1, wherein in step a): reaction 3 comprises adding the 1,1,3,3,-tetramethoxypropane directly to reaction mixture comprising the hydrazine compound of formula (b).

18. Method according to claim 1, wherein in step a), the $M(NO_2)_n$, is $LiNO_2$, $NaNO_2$, or $KNO_2$.

* * * * *